US008604176B2

(12) United States Patent  
Smolke et al.

(10) Patent No.: US 8,604,176 B2  
(45) Date of Patent: Dec. 10, 2013

(54) PROTEIN-RESPONSIVE RNA CONTROL DEVICES AND USES THEREOF

(75) Inventors: Christina D. Smolke, Menlo Park, CA (US); Stephanie J. Culler, Placentia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/943,350

(22) Filed: Nov. 10, 2010

(65) Prior Publication Data

US 2011/0111411 A1 May 12, 2011

Related U.S. Application Data

(60) Provisional application No. 61/259,971, filed on Nov. 10, 2009.

(51) Int. Cl.
| | |
|---|---|
| C07H 21/02 | (2006.01) |
| C07H 21/04 | (2006.01) |
| C12Q 1/68 | (2006.01) |
| A61K 48/00 | (2006.01) |

(52) U.S. Cl.
USPC .......... 536/23.1; 536/24.5; 514/44 R; 435/6.1

(58) Field of Classification Search
None
See application file for complete search history.

(56) References Cited

U.S. PATENT DOCUMENTS

| | | | | |
|---|---|---|---|---|
| 7,312,325 | B2 * | 12/2007 | Sullenger et al. | 536/24.5 |
| 7,563,601 | B1 * | 7/2009 | Gaur | 435/91.1 |
| 2006/0058253 | A1 * | 3/2006 | Chabot et al. | 514/44 |
| 2009/0170793 | A1 * | 7/2009 | Gaur | 514/44 |

OTHER PUBLICATIONS

Serganov et al., Ribozymes, riboswitches and beyond: regulation of gene expression without proteins, 2007, Nature Reviews Genetics, vol. 8, pp. 776-790.*
Cheah et al., Control of alternative RNA splicing and gene expression by eukaryotic riboswitches, 2007, Nature, vol. 447, pp. 497-500.*
Tsutsui et al., Angiopoietin 2 expression in invasive ductal carcinoma of the breast: its relationship to the VEGF expression and microvessel density, 2006, Breast Cancer Research and Treatment, vol. 98, pp. 261-266.*
Ebihara et al., Over-expression of E2F-1 in esophageal squamous cell carcinoma correlates with tumor progression, 2004, Diseases of the Esophagus, vol. 17, pp. 150-154.*
McAlinden et al., Missense and nonsense mutations in the alternatively-spliced exon 2 of COL2A1 cause the ocular variant of Stickler syndrome, 2008, Human Mutation, vol. 29, pp. 83-90.*
Kalinski et al., Differential expression of VEGF-A and angiopoietins in cartilage tumors and regulation by interleukin-1beta, 2006, Cancer, vol. 106, pp. 2028-2038.*
Wang et al., Splicing regulation: From a parts list of regulatory elements to an integrated splicing code, 2008, RNA, vol. 14, pp. 802-813.*
W. Weber, M. Fussenegger, "Engineering of Synthetic Mammalian Gene Networks", Chem Biol 16, 287 (Mar. 27, 2009).
A. S. Khalil, J. J. Collins, "Synthetic biology: applications come of age", Nat Rev Genet 11, 367 (May 2010).
C. J. Bashor, N. C. Helman, S. Yan, W. A. Lim, "Using Engineered Scaffold Interactions to Reshape MAP Kinase Pathway Signaling Dynamics", Science 319, 1539 (Mar. 14, 2008).
M. M. Babu, N. M. Luscombe, L. Aravind, M. Gerstein, S. A. Teichmann, "Structure and evolution of transcriptional regulatory networks", Curr Opin Struct Biol 14, 283 (Jun. 2004).
J. M. Vaquerizas, S. K. Kummerfeld, S. A. Teichmann, N. M. Luscombe, "A census of human transcription factors: function, expression and evolution", Nat Rev Genet 10, 252 (Apr. 2009).
K. H. Link, R. R. Breaker, "Engineering ligand-responsive gene-control elements: lessons learned from natural riboswitches", Gene Ther, (Jul. 9, 2009).
E. A. Davidson, A. D. Ellington, "Synthetic RNA circuits", Nat Chem Biol 3, 23 (Jan. 2007).
B. Suess, J. E. Weigand, "Engineered riboswitches", RNA Biol 5, 24 (Jan.-Mar. 2008).
M. N. Win, J. C. Liang, C. D. Smolke, "Frameworks for Programming Biological Function through RNA Parts and Devices", Chem Biol 16, 298 (Mar. 27, 2009).
F. J. Isaacs et al., "Engineered riboregulators enable post-transcriptional control of gene expression", Nat Biotechnol 22, 841 (Jul. 2004).
B. D. Brown et al., "Endogenous microRNA can be broadly exploited to regulate transgene expression according to tissue, lineage and differentiation state", Nat Biotechnol 25, 1457 (Dec. 2007).
K. Rinaudo et al., "A universal RNAi-based logic evaluator that operates in mammalian cells", Nat Biotechnol 25, 795 (Jul. 2007).
J. Villemaire, I. Dion, S. A. Elela, B. Chabot, "Reprogramming Alternative Pre-messenger RNA Splicing through the Use of Protein-binding Antisense Oligonucleotides", J Biol Chem 278, 50031 (Dec. 12, 2003).
A. D. Ellington, J. W. Szostak, "In vitro selection of RNA molecules that bind specific ligands", Nature 346, 818 (Aug. 30, 1990).
C. Tuerk, L. Gold, "Systematic Evolution of Ligands by Exponential Enrichment: RNA Ligands to Bacteriophage T4 DNA Polymerase", Science 249, 505 (Aug. 3, 1990).

* cited by examiner

*Primary Examiner* — Dana Shin
(74) *Attorney, Agent, or Firm* — McCarter & English, LLP; Elizabeth A. Hanley; Yu Lu

(57) ABSTRACT

The invention described herein relates to an RNA-based control device that senses the presence and/or concentration of at least one protein ligand, preferably through its protein-binding aptamer domain, and regulates a target gene expression through alternative splicing of the target gene in which the RNA-based control device is integrated. The device has uses in therapeutic as well as diagnostic applications.

20 Claims, 17 Drawing Sheets

PROTEIN-RESPONSIVE RNA CONTROL DEVICES AND USES THEREOF

REFERENCE TO RELATED APPLICATIONS

This application claims the benefit of the filing date of U.S. Provisional Application No. 61/259,971, filed on Nov. 10, 2009, the entire content of which, including any drawings, is incorporated herein by reference.

GOVERNMENT SUPPORT

Work described herein was funded, in whole or in part, by R21 CA115471-01 and 1RC1 GM091298-01 from the National Institute of Health (NIH). The United States Government has certain rights in this invention.

BACKGROUND OF THE INVENTION

Cellular decisions, such as differentiation, response to stress, disease progression, and apoptosis, depend on regulatory networks that control enzymatic activities, protein translocation, and genetic responses. Central to the genetic programming of biological systems is the ability to process information within cellular networks and link this information to new cellular behaviors, in essence rewiring network topologies.

Although engineering of gene networks has been attempted before, these engineered gene networks has been limited by a number of factors, including an inability to interface with native components. Therefore, alternative platforms for engineered gene networks that are expected to have widespread applications in basic research, biotechnology, and medicine are still lacking.

SUMMARY OF THE INVENTION

The invention described herein relates to a class of RNA control devices that overcome existing limitations by coupling increased abundance of particular proteins to targeted gene expression events through, for example, the regulation of alternative RNA splicing. Methods and systems of the invention provide a genetic platform that can build programmable sensing-actuation devices that enable autonomous control over cellular behavior. For example, the engineered RNA devices of the invention can detect signaling through the endogenous signaling pathways in human cells, and rewire these pathways to produce new behaviors, thereby linking disease markers to noninvasive sensing and reprogrammed cellular fates.

Thus in one aspect, the invention provides an RNA capable of undergoing alternative splicing in an actuator module, comprising: (1) an input module comprising an aptamer that binds a protein ligand; (2) an output module comprising a coding sequence; and, (3) the actuator module operably connected to the input module and the output module, and comprising a sequence capable of undergoing alternative splicing, wherein the aptamer is integrated at or near a regulatory sequence for alternative splicing, and wherein binding of the protein ligand to the aptamer enhances or inhibits the function of the regulatory sequence to alter alternative splicing pattern and expression of the coding sequence.

Exemplary RNAs of the invention are described in the examples hereinbelow, including all disclosed RNA with their specific sequences, and functional equivalents thereof.

In certain embodiments, the regulatory sequence includes (but are not limited to) a 5' splice site (5' ss), a 3' splice site (3' ss), a splicing branch point, a polypyramidine tract, a splicing enhancer, or a splicing suppressor. For example, the 5' ss includes the consensus GU sequence, the 3' ss includes the consensus AG sequence, the splicing branch point includes the conserved adenine nucleotide, and the polypyramidine tract is rich in C and U ribonucleotides. The enhancer and/or silencer may or may not be located completely within an intron sequence, and can be partly or entirely within an exon sequence. Other sequences that potentially affect alternative splicing pattern are also within the scope of the regulatory sequence.

In certain embodiments, the aptamer is integrated into an intron, such as an intron within the actuator domain. The aptamer may be integrated between 1-150 nucleotides (nts), 1-100 nts, 1-75 nts, 1-50 nts, 2-30 nts, 2-20 nts, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nts away from the regulatory sequence. In certain embodiments, the aptamer may be integrated between a range of nucleotide length, wherein the upper limit of the range may be about 150, 140, 130, 120, 110, 100, 90, 80, 70, 60, 50, 40, 30, 20 nts, and wherein the lower limit of the range may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nts (including any appropriate combinations of the upper and lower limits). In certain embodiments, the preferred integration sequence in the minigene described in the examples include the ten sites used in the examples. Other integration sites, for any intron insertion, include locations corresponding to the ten sites used in the examples. The integration location of the aptamer may be within a range of nucleotides from a nearby regulatory sequence, and the range may have an upper and lower limit using any proper combination of the integers referred to above.

In certain embodiments, the output module is 3' to the actuator module. In a related embodiment, the output module is 5' or upstream of the actuator module.

In certain embodiments, the protein ligand is exogenous to a cell. For example, the ligand may be exogenously added to an environment in which the cell resides (such as in a tissue culture container, or an in vivo environment), although the same protein may also be endogenously produced, for example, under given circumstances. The exogenously added ligand may further contain heterologous sequences, such as a label or tag, e.g., a radioactive label, a fluorescent label, an epitope tag, a nuclear localization signal, a membrane translocation domain (that may be useful for transcytosis), etc.

In certain embodiments, the protein ligand is endogenous to a cell (e.g., a eukaryotic cell, a mammalian cell, a human cell, a non-human mammalian cell). The endogenous ligand is synthesized by the cell, which synthesis may be constitutive or inducible. In either case (constitutive or inducible), the level of expression of the endogenous protein ligand may vary depending on, for example, the presence or absence of an environmental stimuli, or a change in cellular state. Exemplary environmental stimuli include hormones, growth factors, cytokines, change of environmental pH, temperature, osmolarity, salt concentration, change of cell-cell interaction, or any event that triggers signaling.

In certain embodiments, the protein ligand is a transcription factor. In certain embodiments, the protein ligand is not a transcription factor. In certain embodiments, the protein ligand is a nuclear protein. In certain embodiments, the protein ligand localizes to the nucleus. In certain embodiments, the protein ligand contains a nuclear localization signal (NLS), either endogenous NLS or heterologous NLS.

Numerous NLS sequences are known in the art, such as the SV40 large T antigen NLS (PKKKRKV) (see Kalderon et al., Cell 39:499-509, 1984).

In certain embodiments, the expression of the protein ligand or lack thereof is associated with an abnormal or a differentiated state of a cell. For example, the abnormal state (as opposed to a normal, healthy state) may be associated with: a disease condition, over-proliferation of a cell, drug resistance, or abnormal apoptosis.

In certain embodiments, the protein ligand is MS2, NF-κB p50, NF-κB p65, or β-catenin.

In certain embodiments, the actuator module comprises an exon that is either partially or wholly included, or partially or wholly excluded, in the alternative splicing product. The exon may encode a protein domain or motif, the inclusion or exclusion of which alters the function of the product encoded by the coding sequence.

For example, the protein domain may be a transcription activation/suppression domain. Together with a, for example, DNA binding domain encoded by the coding sequence of the output module, the final protein product may be a functional transcription factor if the optional exon is included in the alternative splicing product. In contrast, the final protein product may be without function or becomes a dominant negative mutant protein without the exon in the alternative splicing product.

In certain embodiments, the exon may comprise a sequence element that inhibits the expression of a product encoded by the coding sequence. For example, the sequence element may be any one or more of a translation stop codon, a transcription terminator, a secondary structure that inhibits ribosome function (e.g., scanning), or a self-cleaving ribozyme (e.g., a hammerhead ribozyme).

In certain embodiments, the sequence capable of undergoing alternative splicing is a minigene comprising a first exon, a first intron, a second exon, a second intron, and a third exon in tandem, wherein the second exon is included in one alternative splicing product, but is excluded in a different alternative splicing product. The second exon may comprise a sequence element that inhibits the expression of a product encoded by the coding sequence, such as a translation stop codon, a transcription terminator, a secondary structure that inhibits ribosome function (e.g., scanning), or a self-cleaving ribozyme (e.g., a hammerhead ribozyme). The second exon may encode a protein domain or motif, the inclusion or exclusion of which alters the function of the product encoded by the coding sequence.

In certain embodiments, the RNA may contain modified nucleotides and/or sugar-phosphate backbone. Such a modified RNA may be delivered directly into the cell, e.g., as an exogenous sensor/device with long half-life. To the extent that the modified RNA must be translated or alternatively spliced, the modifications do not negatively impact splicing and/or translation substantially.

Any gene product may be encoded by the coding sequence. In certain embodiments, the coding sequence encodes a reporter protein (e.g., a fluorescent protein), a transcription factor, an enzyme, a proapoptotic protein (e.g., HSV-TK, PUMA), an anti-apoptotic protein, a precursor for siRNA or miRNA (or an RNAse III substrate). In certain embodiments, the encoded gene product (e.g., protein) regulates a specific cellular function of the host cell in response to the expression level of the protein ligand. In certain embodiments, change in the expression level of the protein ligand in the host cell does not normally lead to a change in the expression level of the encoded gene produce.

In a related aspect, the invention provides an RNA capable of undergoing alternative splicing in an actuator module, comprising: (1) a first input module comprising a first aptamer that binds a first protein ligand, and integrated at or near a first regulatory sequence for alternative splicing; (2) a second input module comprising a second aptamer that binds a second protein ligand, and integrated at or near a second regulatory sequence for alternative splicing; (3) an output module comprising a coding sequence; and, (4) the actuator module operably connected to the first and second input modules and the output module, and comprising a sequence capable of undergoing alternative splicing, wherein binding of the first and second protein ligands to their respective aptamers synergistically modulates alternative splicing through modulating the function of the respective regulatory sequences.

In certain embodiments, the first and the second aptamers are different or the same.

In certain embodiments, the first and the second protein ligands are different or the same.

In a related aspect, the invention provides an RNA capable of undergoing alternative splicing in an actuator module, comprising: (1) an input module comprising an aptamer that binds a protein ligand; (2) an output module comprising a coding sequence; and, (3) the actuator module operably connected to the input module and the output module, and comprising a sequence capable of undergoing alternative splicing, wherein the aptamer is integrated at or near a regulatory sequence for alternative splicing, and wherein binding of the protein ligand to the aptamer modulates the function of the regulatory sequence to alter alternative splicing pattern and expression of the coding sequence, and wherein the actuator module comprises the 3-exon-2-intron minigene structure as described herein.

Another aspect of the invention provides a vector or an expression construct encoding any of the RNAs described herein.

Another aspect of the invention provides a cell comprising any of the RNAs, vectors, or expression constructs described herein.

Yet another aspect of the invention provides a method of producing a desired RNA capable of undergoing alternative splicing in an actuator module, the method comprising: (1) providing a candidate RNA comprising: (a) an input module comprising an aptamer that binds a protein ligand; (b) an output module comprising a coding sequence; and, (c) the actuator module operably connected to the input module and the output module, wherein the aptamer is integrated at an integration site that is at or near a regulatory sequence for alternative splicing; (2) contacting each RNA with the protein ligand, under a condition that permits binding of the protein ligand to the aptamer; (3) determining whether binding of the protein ligand to the aptamer integrated at the integration site enhances or inhibits the function of the regulatory sequence in alternative splicing; (4) isolating the candidate RNA as the desired RNA, if binding of the protein ligand to the aptamer either enhances or inhibits the function of the regulatory sequence in alternative splicing.

In certain embodiments, the method further comprises replacing the aptamer with a different aptamer, and repeating steps (2)-(4).

In certain embodiments, the different aptamer binds to the same or a different protein ligand.

In certain embodiments, the method is carried out in vitro (or in vivo).

Another aspect of the invention provides a pharmaceutical preparation or composition, comprising any of the subject RNA, or the vector or expression construct encoding the same, and a pharmaceutically acceptable carrier suitable for administration to a human or non-human subject.

A further aspect of the invention provides a method of modulating the expression of a gene of interest (GOI) in a cell, in response to a change in expression level of a native cellular pathway protein ligand, the method comprising: (1) introducing into the cell an RNA capable of undergoing alternative splicing in an actuator module, said RNA comprising: (a) an input module comprising an aptamer that binds the protein ligand; (b) an output module comprising a coding sequence for the GOI; and, (c) the actuator module operably connected to the input module and the output module, wherein the aptamer is integrated at or near a regulatory sequence for alternative splicing, and wherein binding of the protein ligand to the aptamer modulates the function of the regulatory sequence to alter alternative splicing pattern and expression of the coding sequence; (2) effecting the change in expression level of the protein ligand; thereby modulating the expression of the GOI in the cell.

In certain embodiments, the expression level of the native cellular pathway protein ligand is associated with a disease condition or a differentiated state, and wherein expression of the GOI inhibits the progression or a symptom of the disease condition or differentiated state.

All embodiments described herein, including those in the examples and drawings, are contemplated to be able to combine with any other embodiments unless explicitly excluded.

BRIEF DESCRIPTION OF THE DRAWINGS

FIG. 1 is a schematic drawing showing an alternative splicing-based RNA control device that translates protein inputs to targeted gene expression outputs.

FIG. 2 shows that representative RNA control devices detect endogenous protein inputs and signaling through native pathways.

FIG. 3 shows that the subject RNA devices can implement combinatorial control schemes through multi-input processing.

FIG. 4 shows that the subject RNA devices can detect endogenous markers of disease and trigger targeted cell death.

DETAILED DESCRIPTION OF THE INVENTION

1. Overview

Figure 1A:
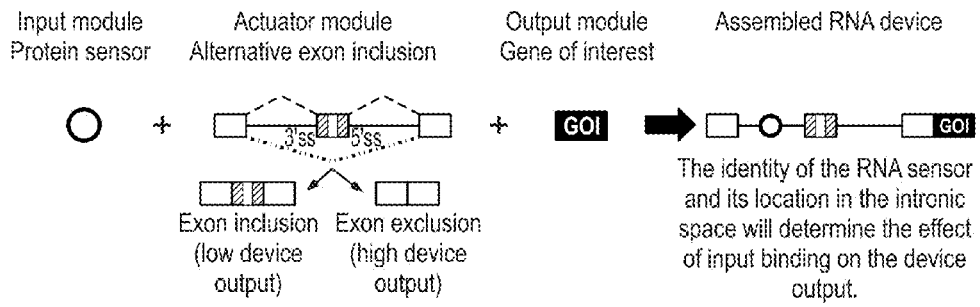
FIG. 1A illustrates platform composition of an RNA control device based on alternative splicing. The input module, consisting of an RNA-based protein sensor or aptamer, detects presence and changes in target nuclear protein concentrations. The sensor transmits information on binding events to the actuator module, which is shown here to consist of a three-exon, two-intron mini-gene, where the alternatively spliced exon contains a stop codon. The actuator controls the expression of the output module, consisting of a gene of interest (GOI). The three modules are physically linked in a transcript to form the assembled RNA control device. The identity of the RNA sensor and its location in the intronic space will determine the effect of input binding on the device output.

The invention described herein is partly based on the discovery that aptamers that bind large molecular weight ligands, such as protein ligands, can be integrated into key locations near sequence elements required for alternative splicing and affect alternative splicing pattern, especially the discovery that such ligands can potentially modulate alternative splicing pattern by either inhibiting or enhancing the function of the sequence elements.

The invention is also partly based on the surprising discovery that, for the same aptamer integration location, depending on the aptamer inserted and/or the protein ligand bound by the aptamer, either inhibitory or enhancement of the function of the alternative splicing sequence elements may be achieved.

In general, the subject RNA comprises a modular actuator domain, a modular input module, and a modular output module, wherein binding of a protein ligand to the aptamer in the input module leads to alternative splicing in the actuator domain, and the expression of the coding sequence. Although the subject RNA is in general single-stranded, it may comprise one or more double-stranded regions (or stems) due to intramolecular interaction (e.g., RNA secondary structure).

In certain embodiments, the subject RNA may comprise one or more modified nucleotides and/or backbone. If one or more phosphodiester linkage between the nucleotides are broken, the folded polynucleotide may in fact be double-stranded while maintaining substantially the same secondary structure.

2. Definition

The "actuator domain" of the invention refers to sequence domain that comprises a sequence capable of undergoing alternative splicing, and thus encodes the system control function.

"Complementary" refers to a nucleotide or nucleotide sequence that hybridizes to a given nucleotide or nucleotide sequence. For instance, for DNA, the nucleotide A is complementary to T, and vice versa, and the nucleotide C is complementary to G, and vice versa. For instance, in RNA, the nucleotide A is complementary to the nucleotide U, and vice versa, and the nucleotide C is complementary to the nucleotide G, and vice versa. Complementary nucleotides include those that undergo Watson and Crick base pairing and those that base pair in alternative modes. For instance, as used herein for RNA, the nucleotide G is complementary to the nucleotide U and vice versa, and the nucleotide A is complementary to the nucleotide G and vice versa. Therefore, in an RNA molecule, the complementary base pairs are A and U, G and C, G and U, and A and G. Other combinations, e.g., A and C, A and A, G and G, or C and U, are considered to be non-complementary base pairs.

A "complementary sequence" comprises individual nucleotides that are complementary to the individual nucleotides of a given sequence, where the complementary nucleotides are ordered such that they will pair sequentially with the nucleotides of the given sequence. Such a complementary sequence is said to be the "complement" of the given sequence.

"Do/does not bind" as used herein to describe aptamer-ligand binding, does not mean that there is absolutely no binding at all. Compared to an aptamer that does bind the ligand (a "binding aptamer"), the $K_{Apt}$ (association constant for binding between ligand and aptamer) for the aptamer that "does not bind" the ligand is at least about 10-fold, 100-fold, 1000-fold or more larger than that of the binding aptamer, and thus its binding affinity for the ligand is at least about 10-fold, 100-fold, 1000-fold or more weaker than that of the binding aptamer.

"Framework" refers to a basic conceptual structure that is used to solve a complex product design issue. As used here, the framework is used to reliably design and construct specific instances of the subject RNA.

"Modular" refers to a property of a system composed of modules that indicates whether the modules can by interchanged as parts without changing the interface between modules or the modules themselves.

"Module" refers to a self-contained system component that has a well defined interface with other system components.

"Nucleotide" refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine, 6-mercaptopurine, 5-fluorouracil, 5-iodo-2'-deoxyuridine and 6-thioguanine, cytosine exocyclic amines, substitution of 5-bromo-uracil, backbone modifications, methylations, and unusual base-pairing combinations. Additional analogs include at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

"Nucleic acid," "nucleic acid sequence," "nucleic acid molecule," and "polynucleotide" refer to a DNA sequence or analog thereof, or an RNA sequence or analog thereof. Nucleic acids are formed from nucleotides, including, but not limited to, the nucleotides listed above.

Other terms used herein and in the claims adopt their plain meanings as would have been understood by one of skill in the relevant art, that are not inconsistent with the usages in the instant specification.

The section headings used herein are for organizational purposes only, and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

It will be appreciated that there is an implied "about" prior to any numeric values, such as temperatures, concentrations, amino acid/polynucleotide sequence lengths, times, etc. discussed in the present teachings, such that slight and insubstantial (such as less than 5%) deviations are within the scope of the present teachings herein. In this application, the use of the singular includes the plural unless specifically stated otherwise. Also, the use of "comprise," "comprises," "comprising," "contain," "contains," "containing," "include," "includes," "including," and "having" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

3. Aptamers

An "aptamer" may be a nucleic acid molecule, such as RNA or DNA (typically RNA), that is capable of binding to a specific molecule with high affinity and specificity (Ellington et al., Nature 346: 818-22, 1990; and Tuerk et al., Science 249: 505-10, 1990). Although aptamer in general can bind a wide variety of exemplary ligands, including, without limitation, small molecules, such as drugs, metabolites, intermediates, cofactors, transition state analogs, ions, metals, nucleic acids, polysaccharides, glycoproteins, hormones, receptors and cell surfaces (such as cell walls and cell membranes), and toxins, aptamers that may be used in the instant invention bind proteins or polypeptides.

An aptamer will most typically have been obtained by in vitro selection for binding of a target molecule (e.g., a protein ligand). However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants ($K_d$) of the aptamer for its ligand as compared to the dissociation constant of the aptamer for other materials in the environment or unrelated molecules in general. A ligand is one which binds to the aptamer with greater affinity than to unrelated material. Typically, the $K_d$ for the aptamer with respect to its ligand will be at least about 10-fold less than the $K_d$ for the aptamer with unrelated material or accompanying material in the environment. Even more preferably, the $K_d$ will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

The terms "nucleic acid molecule" and "polynucleotide" refer to deoxyribonucleotides or ribonucleotides and polymers thereof in either single- or double-stranded form. The term "RNA" (such as the RNA comprising one or more aptamers) refers to ribonucleic acid, preferably in single-stranded form. Unless specifically limited, the terms encompass nucleic acids/RNAs containing known analogues of natural nucleotides which have similar binding properties as the reference nucleic acid and are metabolized in a manner similar to naturally occurring nucleotides. The terms may also encompass nucleic acids/RNAs containing chemical modifications, such as modifications at the base moiety, sugar moiety, and/or phosphate backbone, that tend to increase stability or half-life of the molecules in vivo. For example, these molecules may have naturally occurring phosphodiester linkages, as well as those having non-naturally occurring linkages, e.g., for stabilization purposes, or for enhancing hydrophobic interaction with protein ligands.

Exemplary modified base moiety may be selected from the group including, but not limited to: 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

Exemplary modified sugar moiety may be selected from the group including but not limited to arabinose, 2-fluoroarabinose, xylulose, and hexose.

Exemplary neutral peptide-like backbone modification include: peptide nucleic acid (PNA) (see, e.g., in Perry-O'Keefe et al. (1996) Proc. Natl. Acad. Sci. USA 93:14670 and in Eglom et al. (1993) Nature 365:566), or modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The nucleic acid may be in any physical form, e.g., linear, circular, or supercoiled.

The aptamer of the invention can be comprised entirely of RNA. In other embodiments of the invention, however, the aptamer can instead be comprised entirely of DNA, or partially of DNA, or partially of other nucleotide analogs. Such aptamer RNAs may be introduced into a cell as a DNA that encodes the aptamer such that transcription results in the aptamer-regulated RNA. Alternatively, an aptamer-regulated RNA itself can be introduced into a cell.

Aptamers are typically developed to bind particular ligands by employing known in vivo or in vitro (most typically, in vitro) selection techniques known as SELEX (Ellington et al., Nature 346: 818-22, 1990; and Tuerk et al., Science 249, 505-10, 1990). Methods of making aptamers are also described in, for example, US-2009-0082217-A1, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions, preferably conditions found in the nucleus.

Nucleic acids or RNAs of the invention may also be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. Nucl. Acids Res. 16:3209 (1988)), methylphosphonate oligonucleotides can be prepared by use of controlled pore glass polymer supports (Sarin et al., Proc. Natl. Acad. Sci. USA 85:7448-7451 (1988)), etc.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand. For example, US-2009-0082217-A1 describes a CE based efficient selection scheme for aptamer that binds any ligand, including protein ligands and small molecule ligands, preferably in the context of a switch platform, or surrounding polynucleotide sequences in which the aptamer is expected to be function.

For an aptamer suitable for use in the present invention, the binding affinity of the aptamer for the ligand may be tunable or variable, such that different aptamers for the same ligand may be chosen to provide the desired level of aptamer-ligand binding. For example, the association constant for the aptamer and its associated ligand may be chosen such that the ligand functions to bind to the aptamer and have the desired effect at the concentration of ligand obtained upon administration/expression of the ligand. For in vivo use, for example, the association constant may be chosen such that binding occurs well below the maximum concentration of ligand that can be achieved in the nucleus.

4. Actuator Module

The actuator module of the invention is operably connected to the input module and the output module, and comprising a sequence capable of undergoing alternative splicing. The aptamer of the invention may be integrated within the actuator module, e.g., at or near a regulatory sequence for alternative splicing, and wherein binding of the protein ligand to the aptamer modulates (e.g., inhibits or enhances) the function of the regulatory sequence to alter alternative splicing pattern and expression of the coding sequence.

Many different configurations of the actuator modules may be possible.

For example, as shown in the examples, the actuator module may comprise a 3-exon-2-intron minigene structure (exon 1-intron 1-exon 2-intron 2-exon 3), wherein alternative splicing, depending on the presence or absence of the protein ligand as sensed by the input module, causes the middle exon to be either included or excluded from the final splicing product. The presence of absence of the middle exon may lead to a change in activity for the encoded gene product (e.g., a protein).

In one embodiment, the middle exon includes a negative regulator, such as a stop codon, a translation inhibitor, etc., that inhibits the function of the encoded gene product, or simply prevent the encoded gene product to be produced at all.

In another embodiment, the middle exon includes a positive regulator, such as a protein domain or motif that confers a new or an alter function to the encoded gene product.

Numerous other configurations or variations of the alternatively spliced actuator domains are also possible. For instance, even for the same minigene design, either exon 1 or exon 2 (but not both) may be included in the final encoded product, and each exon may encode different functional domains (e.g., different DNA binding domains that can be linked to the same transcription activation/suppressor domain, such that the alternative splicing products may encode different transcription factors with distinct target genes).

In certain embodiments, 2, 3, 4, 5, 6, 7, 8, or more exons may be present in the actuator domain.

5. Delivery

RNA or nucleic acid molecules of the invention can be delivered to target cells in vivo. A number of methods have been developed for delivering nucleic acids into cells; e.g., they can be injected directly into the tissue site, or modified nucleic acids, designed to target the desired cells can be administered systematically.

Another approach utilizes a recombinant DNA construct in which the RNA or other aptamer-containing nucleic acid is placed under the control of a strong pol III or pol II promoter. The use of such a construct to transfect target cells in the patient will result in the transcription of sufficient amounts of the subject RNA. For example, a vector or expression construct can be introduced in vivo such that it is taken up by a target cell and directs the transcription of a subject RNA. Such a vector or expression construct can remain episomal or become chromosomally integrated, as long as it can be transcribed to produce the desired product. Such vectors can be constructed by recombinant DNA technology methods standard in the art.

Vectors can be plasmid, viral, or others known in the art, used for replication and expression in mammalian cells. A promoter may be operably linked to the sequence encoding the subject RNA. Expression of the subject encoded sequences can be by any promoter known in the art to act in mammalian, preferably human cells. Such promoters can be inducible or constitutive. Such promoters include but are not limited to: the SV40 early promoter region (Bernoist and Chambon, Nature 290:304-310 (1981)), the promoter contained in the 3' long terminal repeat of Rous sarcoma virus (Yamamoto et al., Cell 22:787-797 (1980)), the herpes thymidine kinase promoter (Wagner et al., Proc. Natl. Acad. Sci. USA 78:1441-1445 (1981)), the regulatory sequences of the metallothionine gene (Brinster et al, Nature 296:3942 (1982)), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

Thus the invention also provides an expression vector or construct having a coding sequence that is transcribed to produce one or more transcriptional products that produce a subject RNA in the treated cells. Expression vectors appropriate for producing an aptamer-regulated nucleic acid are well-known in the art. For example, the expression vector is selected from an episomal expression vector, an integrative expression vector, and a viral expression vector.

In certain embodiments, the expression vector can be designed to include one or more subject RNA an RNA transcript, such as in the 3' untranslated region (3'-UTR), so as to regulate transcription, stability and/or translation of that RNA transcript in a manner dependent on the ligand. To further illustrate, the expression construct can include a coding sequence for a polypeptide such that the mRNA transcript includes both the polypeptide coding sequence as well as one or more of the RNA of the invention. In this way, expression of the polypeptide can be rendered dependent on the ligand(s) to which the aptamer(s) bind.

6. Exemplary Formulations

The subject RNA or nucleic acids may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject RNA or nucleic acids can be provided in formulations also including penetration enhancers, carrier compounds and/or transfection agents.

Representative United States patents that teach the preparation of such uptake, distribution and/or absorption assisting formulations which can be adapted for delivery of the subject RNA or nucleic acid molecules include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The subject RNA or nucleic acids may also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to RNAs or nucleic acids and pharmaceutically acceptable salts, and other bioequivalents.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66,1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Other formulations, delivery methods, and routes of administration are also provided, such as those described in U.S. Pat. App. Publication No. 20040063654.

7. Exemplary Uses

The subject RNA or nucleic acids can further be used to engineer novel regulatory pathways and control loops for applications in metabolic engineering (Khosla et al., Nat Rev Drug Discov 2, 1019-25 (2003)) and synthetic circuit design (Kobayashi et al., Proc Natl Acad Sci USA 101, 8414-9 (2004)) by enabling the cell to sense and respond to intracellular metabolite levels and environmental signals, such as concentration changes in a native cellular pathway protein ligand. Because the activity of the subject RNA or nucleic acids may be tunable over a range of protein ligand concentrations, the system can be designed to inhibit or activate genes only when certain triggering protein ligands have exceeded or gone below certain threshold concentrations. Balancing heterologous gene expression in biosynthetic pathways (Berens et al., Bioorg Med Chem 9, 2549-56 (2001)) to maximize product yield can be achieved with the subject RNA or nucleic acids that regulate expression of any gene of interest in response to any pre-determined pathway intermediates, including any disease markers. Synthetic gene circuits have recently been used to understand and model cellular networks (Nagai et al., Nat Biotechnol 20, 87-90 (2002)) and to achieve cellular control as a step towards "programmable" cell behavior (Watkins et al., Curr Opin Mol Ther 4, 224-8 (2002)). Gene circuits can be built using combinations of the subject RNA or nucleic acids as regulators for precise control schemes. The subject RNA or nucleic acids will be useful tools in building and characterizing circuits that accurately model natural regulatory pathways and yield further insight into these prevalent regulation schemes.

Finally, aptamer-regulated nucleic acids present new tools for cellular imaging (by, for example, using a fluorescent reporter gene as the gene of interest), measuring, and detection strategies enabling programmable concentration-specific detection of intracellular molecules. The subject RNA or nucleic acids offer a unique platform to create tailor-made cellular sensors and "smart" regulators that potentially can target any gene in response to any target ligand, creating new avenues for cellular control and engineering.

EXAMPLES

The invention described herein provides exemplary alternative platforms for constructing sensing-actuation devices based on the detection of broad classes of proteins, and has widespread applications in basic research, biotechnology, and medicine. Several non-limiting, illustrative embodiments of the invention are described in the examples below. These illustrative embodiments of the subject RNA-based devices are not limiting in any respect. However, certain features of the devices may have general applicability.

Example 1

Construction of Protein-Responsive RNA-Based Regulatory Devices

Described herein are protein-responsive RNA-based regulatory devices that integrate protein-binding RNA aptamers into key intronic locations of an alternatively spliced transcript. The devices are capable of linking intracellular protein concentrations to gene expression events.

Figure 1B:
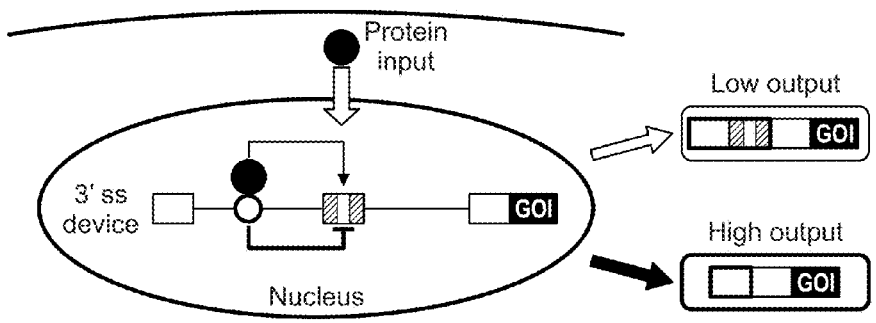
FIG. 1B illustrates a potential mechanism of action for the subject RNA device. Here, a 3' splice site (ss) device is shown, where the input module is located in the intron upstream of the alternative exon, and binding of the protein input to the sensor alters the splicing pattern by either enhancing (arrow line) or suppressing (bar-end line) alternative exon inclusion. Exclusion of the alternative exon results in removal of the stop codon upstream of the GOI, thereby increasing the gene expression output from the device ("high output"). Inclusion of the alternative exon results in reduction or even elimination of GOI expression due to the presence of the upstream stop codon, thereby decreasing gene expression output from the device ("low output").

In general, an exemplary regulatory platform of the invention contains (1) an output module, (2) an actuator module, and (3) an input module. The output module comprises a gene of interest (GOI), such as a reporter gene or a protein having a specific function. The output module is placed downstream of the actuator module, which may comprise a three-exon, two-intron mini-gene in which the middle exon is alternatively spliced, or excluded (FIG. 1A). The middle exon contains a stop codon, such that expression of the GOI is high when the exon is excluded. Control of the device is exerted by the input module, which may comprise an RNA aptamer that senses changes in nuclear protein concentrations, whereby ligand binding to the aptamer alters the splicing pattern, likely through steric hindrance or recruitment of components involved in spliceosome site (ss) recognition (FIGS. 1A & 1B) (Matlin et al., *Nat Rev Mol Cell Biol* 6, 386, 2005).

Specifically, the SMN1-GFP mini-gene fusion plasmid (pCS1773) was constructed through PCR amplification, digestion and ligation in the appropriate expression vector. A region encompassing the last nine nucleotides of exons 6 through the first 21 nucleotides of exon 8 of the SMN1 mini-gene (Culler et al., *Nucleic Acids Res,* 38, 5152, 2010) was amplified through PCR from template pCS1774 with primers Ex6 and Ex8 and PfuUltra II fusion high-fidelity DNA polymerase (Stratagene), and the resulting PCR product was digested with NheI. The SMN1 mini-gene DNA synthesis was performed by DNA 2.0 to contain restriction sites KpnI, EcoRV, ClaI (positions −87, −61 and −50 from 3' ss of exon 7, respectively) and XhoI, HindIII, BamHI and XbaI (positions +10, +50, +70 and +97 from 5' ss of exon 7, respectively). The GFP gene was amplified from the template pKW430 (Stade et al., *Cell* 90, 1041, 1997) with primers GFP1 and GFP2. The resulting PCR product was digested with ApaI and NheI and ligated into the corresponding restriction sites of the mammalian expression vector pcDNA5/FRT (Invitrogen). The SMN1 mini-gene PCR product was then ligated into the NheI restriction site of the resulting GFP construct, to construct the base plasmid SMN1-GFP.

The aptamer sequences used in the examples are CGTACACCATCAGGGTACG (Villemaire et al., *J Biol Chem* 278, 50031, 2003) for MS2; CGTACCCATCAGGGTACG (lacks a bulged adenosine required for MS2 binding) (Villemaire et al., *J Biol Chem* 278, 50031, 2003; Carey et al., *Biochemistry* 22, 4723, 1983) for MS2Δ; AGGCCGATCTATGGACGCTATAGGCACACCGGATACTTTAACGATTGGCT (Lee et al., *Cancer Res* 66, 10560, 2006) for β-catenin; TCGGTTAGCAATTTCATAGGCCACACGGATATCG-CAGGTATCTAGC CGGA (reverse compliment) for β-cateninΔ; GCATCCTGAAACTGTTTTAAGGTTGGC-CGA TGC (Chan et al., *Nucleic Acids Res* 34, e36, 2006) for NF-κB p50(1); CGTAGCCGGTTGGAATTTTGT-CAAAGTCCTACG (reverse compliment) for NF-κB p50(1)Δ and p50(2)Δ; GATCTTGAAACTGTTTTAAGGTTG-GCCGA TC (Mi et al., *Nucleic Acids Res* 34, 3577, 2006) for NF-κB p50(2); GAAGCTTACAAGAAGGACAGCAC-GAATAAAACCTGCGTAA ATCCGCCCCATTTGTG-TAAGGGTAGTGGGTCGAATTCCGCTCA (Wurster & Maher, 3rd, *Rna* 14, 1037, 2008) for NF-κB p65; and ACTCGCCTTAAGCTGGGTGATGGGAAT-GTGTTTACCCCGCCTAAATGCGTCCAAAAT AAG-CACGACAGGAAGAACATTCGAAG (reverse compliment) for NF-κB p65Δ.

Since gene expression can be sensitive to a myriad of external factors, appropriate controls may be required to account for potential nonspecific effects of experimental procedures applied to cells. For example, gene expression activity measured through fluorescent reporters can be altered through nonspecific effects of the ligand on gene expression or cellular fluorescence through other cellular mechanisms. Therefore, in the examples described herein, careful controls were used in the examples to ensure accurate accounting of any nonspecific effects of heterologous protein expression or exogenous ligand addition (when inducing pathway signaling) on gene expression and phenotypic responses (e.g., cell survival and death).

Thus for each aptamer-containing device, a corresponding inactive sensor control (negative control) was constructed in which the wild-type aptamer was replaced by a mutated aptamer, such that the only difference between the device and its corresponding control was its ability to bind to its corresponding ligand. As such, measuring the difference in gene expression (or other measure of output activity) in the presence and absence of ligand for the negative control provides a measure of nonspecific effects of the ligand. The same measurement for the wild-type aptamer device provides a combined measure of specific and nonspecific effects of the ligand on the measured device output.

To account for the non-aptamer-mediated effects of the ligand, the fold-change (ratio of signal in the presence and absence of ligand) of the wild-type device was normalized to that of the negative control. As it is assumed that the nonspecific effects of the ligand will be similar for a device containing a wild-type aptamer and its negative control, this value provides a measure of the specific effects of ligand binding to the sensor element on the gene regulatory output of the device. The validity of such normalization methods for ligand-mediated gene-regulatory systems has been described elsewhere (Chen et al., *Proc Natl Acad Sci USA,* 107, 8531, 2010). Such a measure may be particularly useful in systems where the addition of molecules that activate pathway signaling (i.e., TNF-α, LTD$_4$) may have significant nonspecific effects on cellular fluorescence, gene expression, or other cellular mechanisms.

A list of the primer sequences used in the examples are summarized in the table below (the "primer sequence table").

| Name | Primer sequence (5' to 3') |
|---|---|
| Ex6 | GCGCGCTAGCATGTATTATATGGTAAGTAATCACTCAGC |
| Ex8 | ATAGCTAGCGCTGCTACCTGCCAGC |
| GFP1 | GCGCGCTAGCGTGAGCAAGGGCGAG |
| GFP2 | GCGCGGGCCCTTAGTACAGCTCGTCCATGCC |
| Puma1 | ATAGTTTAAACGGTGGTTCT GGTGGTTCTGCCCGCGCACGCCAGGAG |

-continued

| Name | Primer sequence (5' to 3') |
|---|---|
| Puma2 | GCGC GTTTAAACTTAATTGGGCTCCATCTCGGG |
| TK1 | GCGCGCTAGCGTGACAGGGGGAATGGC |
| TK2 | GCGCGTTTAAACTTAGTTAGCCTCCCCCATCTC |
| DsRed1 | ATAGGATCCGACAACACCGAGGACGTCAT |
| DsRed2 | ATAGCGGCCGCCTACTGGGAGCCGGAG |
| MS2-1 | AGCCAAAAAAAAACGCAAAGTGGCTTCTAACTTTACTCAGTTCGTTC |
| MS2-2 | ATAGGATCCACCACCACCACCGTAGATGCCG |
| MS2-3 | ATAGGTACCATGGATTACAAGGATGACGATGACAAGCCAAAAAAAAA CGCAAAGTGGCTTCTAACTTTAC |
| P50-1 | AGCCAAAAAAAAAACGCAAAGTGGCAGAAGATGATCCATATTTGGGAA G |
| P50-2 | ATAGGTACCGTCATCACTTTTGTCACAACCTTC |
| P50-3 | ATAGCTAGCATGGATTACAAGGATGACGATGACAAGCCAAAAAAAAA CGCAAAGTGGCAGAAGATGATCC |
| SMN1c DNA | TAGAAGGCACAGTCGAGG |
| Bcat3 | ATATGATACTAGCTATCAGGCCGA |
| Bcat3Δ | ATATGATATCTAGCTATCTCGGTTAG |
| Bcat6 | ATATATCGATGTCTATATAGCTATTTTTTTTAACTT |
| Bcat6Δ | ATATATCGATGTCTATATAGCTATTTTTTTTAACTT |
| AptRv | ATACTCGAGCAGACTTACTCCTTAATTTAAGGAATG |
| p50(1) | ATATGATATCTAGCTATCCGCGC |
| p50(1)Δ | ATATGATATCTAGCTATCCGTAGCC |
| p50(2) | ATATGATATCTAGCTATCCGCGC |
| p65 | ATATGATATCTAGCTATCGAAGCTACAAGAAGGACAGCAC |

A list of the plasmids used in the examples are summarized in the table below (the "plasmid table").

| Name | Description |
|---|---|
| pCS1773 | SM1-GFP. Contains the wild-type SMN1 mini-gene fused to the C-terminus of GFP. |
| pCS1774 | SMN1 mini-gene template. |
| pCS1775 | β-cat-3-GFP. Wild-type SMN1 mini-gene containing the β-catenin aptamer in position 3 of intron 6 fused to the C-terminus of GFP. |
| pCS1776 | β-catΔ-3-GFP. Wild-type SMN1 mini-gene containing the mutant β-catenin aptamer in position 3 of intron 6 fused to the C-terminus of GFP. |
| pCS1777 | β-cat-6-GFP. Wild-type SMN1 mini-gene containing the β-catenin aptamer in position 6 of intron 6 fused to the C-terminus of GFP. |
| pCS1778 | β-catΔ-6-GFP. Wild-type SMN1 mini-gene containing the mutant β-catenin aptamer in position 6 of intron 6 fused to the C-terminus of GFP. |
| pCS1779 | NF-κBp50(1)-3-GFP. Wild-type SMN1 mini-gene containing the NF-κBp50(1) aptamer in position 3 of intron 6 fused to the C-terminus of GFP. |
| pCS1780 | NF-κBp50(1) Δ-3-GFP. Wild-type SMN1 mini-gene containing the mutant NF-κBp50(1) aptamer in position 3 of intron 6 fused to the C-terminus of GFP. |
| pCS1781 | NF-κBp50(2)-3-GFP. Wild-type SMN1 mini-gene containing the NF-κBp50(2) aptamer in position 3 of intron 6 fused to the C-terminus of GFP. |
| pCS1782 | NF-κBp65-3-GFP. Wild-type SMN1 mini-gene containing the NF-κBp65 aptamer in position 3 of intron 6 fused to the C-terminus of GFP. |
| pCS1783 | NF-κBp65 Δ-3-GFP. Wild-type SMN1 mini-gene containing the mutant NF-κBp65 aptamer in position 3 of intron 6 fused to the C-terminus of GFP. |

-continued

| Name | Description |
|---|---|
| pCS1784 | MS2-3-MS2-10. Wild-type SMN1 mini-gene containing the MS2 aptamer in position 3 of intron 6 and in position 10 of intron 7 fused to the C-terminus of GFP. |
| pCS1785 | MS2Δ-3-MS2-10. Wild-type SMN1 mini-gene containing the mutant MS2 aptamer in position 3 of intron 6 and the wild-type MS2 aptamer in position 10 of intron 7 fused to the C-terminus of GFP. |
| pCS1786 | MS2-3-MS2Δ-10. Wild-type SMN1 mini-gene containing the wild-type MS2 aptamer in position 3 of intron 6 and the mutant MS2 aptamer in position 10 of intron 7 fused to the C-terminus of GFP. |
| pCS1787 | MS2Δ-3-MS2Δ-10. Wild-type SMN1 mini-gene containing the mutant MS2 aptamer in position 3 of intron 6 and in position 10 of intron 7 fused to the C-terminus of GFP. |
| pCS1788 | NF-κBp65-3-MS2-10. Wild-type SMN1 mini-gene containing the NF-κBp65 aptamer in position 3 of intron 6 and the MS2 aptamer in position 10 of intron 7 fused to the C-terminus of GFP. |
| pCS1789 | NF-κBp65Δ-3-MS2-10. Wild-type SMN1 mini-gene containing the mutant NF-κBp65 aptamer in position 3 of intron 6 and the MS2 aptamer in position 10 of intron 7 fused to the C-terminus of GFP. |
| pCS1790 | NF-κBp65-3-MS2Δ-10. Wild-type SMN1 mini-gene containing the NF-κBp65 aptamer in position 3 of intron 6 and the mutant MS2 aptamer in position 10 of intron 7 fused to the C-terminus of GFP. |
| pCS1791 | NF-κBp65Δ-3-MS2Δ-10. Wild-type SMN1 mini-gene containing the mutant NF-κBp65 aptamer in position 3 of intron 6 and the mutant MS2 aptamer in position 10 of intron 7 fused to the C-terminus of GFP. |
| pCS1792 | Puma. Contains Puma in pcDNA5/FRT. |
| pCS1793 | MS2-3. Wild-type SMN1 mini-gene containing the MS2 aptamer in position 3 of intron 6 fused to the C-terminus of GFP. |
| pCS1794 | MS2Δ-3. Wild-type SMN1 mini-gene containing the mutant MS2 aptamer in position 3 of intron 6 fused to the C-terminus of Puma. |
| pCS1795 | MS2-3-Puma. Wild-type SMN1 mini-gene containing the MS2 aptamer in position 3 of intron 6 fused to the C-terminus of Puma. |
| pCS1796 | MS2Δ-3-Puma. Wild-type SMN1 mini-gene containing the mutant MS2 aptamer in position 3 of intron 6 fused to the C-terminus of Puma. |
| pCS1797 | β-cat-6-Puma. Wild-type SMN1 mini-gene containing the β-catenin aptamer in position 6 of intron 6 fused to the C-terminus of Puma. |
| pCS1798 | β-catΔ-6-Puma. Wild-type SMN1 mini-gene containing the mutant β-catenin aptamer in position 6 of intron 6 fused to the C-terminus of Puma. |
| pCS1799 | p65-3-Puma. Wild-type SMN1 mini-gene containing the NF-κB p65 aptamer in position 3 of intron 6 fused to the C-terminus of Puma. |
| pCS1800 | p65Δ-3-Puma. Wild-type SMN1 mini-gene containing the mutant NF-κB p65 aptamer in position 3 of intron 6 fused to the C-terminus of Puma. |
| pCS1801 | HSV-TK. Contains HSV-TK in pcDNA5/FRT. |
| pCS1802 | β-cat-6-TK. Wild-type SMN1 mini-gene containing the β-catenin aptamer in position 6 of intron 6 fused to the C-terminus of HSV-TK. |
| pCS1803 | β-catΔ-6-TK. Wild-type SMN1 mini-gene containing the mutant β-catenin aptamer in position 6 of intron 6 fused to the C-terminus of HSV-TK. |
| pCS1804 | p65-3-TK. Wild-type SMN1 mini-gene containing the NF-κB p65 aptamer in position 3 of intron 6 fused to the C-terminus of HSV-TK. |
| pCS1805 | p65Δ-3-TK. Wild-type SMN1 mini-gene containing the mutant NF-κB p65 aptamer in position 3 of intron 6 fused to the C-terminus of HSV-TK. |
| pCS1392 | MS2-DsRed. Contains the FLAG-NLS-MS2 gene fused to the C-terminus of DsRed. |
| pCS1806 | NF-κBp50-DsRed. Contains the FLAG-NLS-NF-κBp50 gene fused to the C-terminus of DsRed. |
| pCS1807 | MS2-Venus. Contains the FLAG-NLS-MS2 gene fused to the C-terminus of Venus. |
| pCS1808 | Venus. Contains Venus in pcDNA5/FRT. |

Aptamer cassette sequences used in the construction of the RNA devices are listed in the table below (the "aptamer cassette sequence table"). Aptamer sequences are italicized, and nucleotides added for strengthening aptamer secondary structure are underlined.

| Name | Position | Restriction sites | Cassette (5'-3') |
|---|---|---|---|
| MS2-1 | 1 | Kpn I/Cla I | ATATGGTACCAACA*CGTACACCATCAGGGTA CGT*CCATATAAAGCTATAGATATCTAGCTA TCGATATAT |

-continued

| Name | Position | Restriction sites | Cassette (5'-3') |
|---|---|---|---|
| MS2Δ-1 | 1 | Kpn I/Cla I | ATATGGTACCAACA*CGTACCCATCAGGGTAC**GTC*CATATAAAGCTATAGATATCTAGCTATCGATATAT |
| MS2-2 | 2 | Kpn I/Cla I | ATATGGTACCAACATCCATATAAAGCTATC*GTACACCATCAGGGTAC*GAGATATCTAGCTATCGATTAT |
| MS2Δ-2 | 2 | Kpn I/Cla I | ATATGGTACCAACATCCATATAAAGCTATC*GTACCCATCAGGGTAC*GAGATATCTAGCTATCGATTAT |
| MS2-3 | 3 | Eco RV/Xho I | ATATGATATCTAGCTATC*CGTACACCATCAGGGTACG*GATGTCTATATAGCTATTTTTTTAACTTCCTTTATTTTCCTTACAGGGTTTCAGACAAAATCAAAAGAAGGAAGGTGCTCACATTCCTTAAATTAAGGAGTAAGTCTGCTCGAGATAT |
| MS2Δ-3 | 3 | Eco RV/Xho I | ATATGATATCTAGCTATC*CGTACCCATCAGGGTACG*GATGTCTATATAGCTATTTTTTTAACTTCCTTTATTTTCCTTACAGGGTTTCAGACAAAATCAAAAGAAGGAAGGTGCTCACATTCCTTAAATTAAGGAGTAAGTCTGCTCGAGATAT |
| MS2-4 | 4 | Cla I/Xho I | ATATATCGATGTCTATATAGCT*CGTACACCATCAGGGTACG*ATTTTTTTAACTTCCTTTATTTTCCTTACAGGGTTTCAGACAAAATCAAAAAGAAGGAAGGTGCTCACATTCCTTAAATTAAGGAGTAAGTCTGCTCGAGATAT |
| MS2Δ-4 | 4 | Cla I/Xho I | ATATATCGATGTCTATATAGCT*CGTACCCATCAGGGTACG*ATTTTTTTAACTTCCTTTATTTTCCTTACAGGGTTTCAGACAAAATCAAAAAGAAGGAAGGTGCTCACATTCCTTAAATTAAGGAGTAAGTCTGCTCGAGATAT |
| MS2-5 | 5 | Cla I/Xho I | ATATATCGATGTCTATATAGCTATTTTTTTTAACTTC*CGTACACCATCAGGGTACG*CTTTATTTTCCTTACAGGGTTTCAGACAAAATCAAAAAGAAGGAAGGTGCTCACATTCCTTAAATTAAGGAGTAAGTCTGCTCGAGATAT |
| MS2Δ-5 | 5 | Cla I/Xho I | ATATATCGATGTCTATATAGCTATTTTTTTTAACTTC*CGTACCCATCAGGGTACG*CTTTATTTTCCTTACAGGGTTTCAGACAAAATCAAAAAGAAGGAAGGTGCTCACATTCCTTAAATTAAGGAGTAAGTCTGCTCGAGATAT |
| MS2-6 | 6 | Cla I/Xho I | ATATATCGATGTCTATATAGCTATTTTTTTTAACTTCCTTTATTTTCCTTAC*CGTACACCATCAGGGTACG*AGGGTTTCAGACAAAATCAAAAAGAAGGAAGGTGCTCACATTCCTTAAATTAAGGAGTAAGTCTGCTCGAGATAT |
| MS2Δ-6 | 6 | Cla I/Xho I | ATATATCGATGTCTATATAGCTATTTTTTTTAACTTCCTTTATTTTCCTTAC*CGTACCCATCAGGGTACG*AGGGTTTCAGACAAAATCAAAAAGAAGGAAGGTGCTCACATTCCTTAAATTAAGGAGTAAGTCTGCTCGAGATAT |
| MS2-7 | 7 | Cla I/Xho I | ATATATCGATGTCTATATAGCTATTTTTTTTAACTTCCTTTATTTTCCTTACAGGGTTTCAGACAAAATCAAAAGAAGGAAGGTGCTCACATTCCTTAAATTAAGGAGTAAGTCTG*CGTACACCATCAGGGTACG*CTCGAGATAT |
| MS2Δ-7 | 7 | Cla I/Xho I | ATATATCGATGTCTATATAGCTATTTTTTTTAACTTCCTTTATTTTCCTTACAGGGTTTCAGACAAAATCAAAAGAAGGAAGGTGCTCACATTCCTTAAATTAAGGAGTAAGTCTG*CGTACCCATCAGGGTACG*CTCGAGATAT |
| MS2-8 | 8 | Xho I/HindIII | ATATCTCGAGCCAGCATTA*CGTACACCATCAGGGTACG*TGAAAGTGAATCTTACTTTTGTAAAAAAGCTTATAT |

-continued

| Name | Position | Restriction sites | Cassette (5'-3') |
|---|---|---|---|
| MS2Δ-8 | 8 | Xho I/HindIII | ATATCTCGAGCCAGCATTA*CGTACCCATCAG GGTACG*TGAAAGTGAATCTTACTTTTGTAAA AAAGCTTATAT |
| MS2-9 | 9 | Xho I/HindIII | ATATCTCGAGCCAGCATTATGAAAGTGAAT CTTA*CGTACACCATCAGGGTACGC*TTTTGTAA AAAGCTTATAT |
| MS2Δ-9 | 9 | Xho I/HindIII | ATATCTCGAGCCAGCATTATGAAAGTGAAT CTTA*CGTACCCATCAGGGTACGC*TTTTGTAA AAAGCTTATAT |
| MS2-10 | 10 | Xho I/Bam HI | ATATCTCGAGCCAGCATTATGAAAGTGAAT CTTACTTTTGTAAAAAAGC*CGTACACCATCA GGGTACG*TTCTTTATGGTTTGTGGGATCCAT AT |
| MS2Δ-10 | 10 | Xho I/Bam HI | ATATCTCGAGCCAGCATTATGAAAGTGAAT CTTACTTTTGTAAAAAAGC*CGTACCCATCAG GGTACG*TTCTTTATGGTTTGTGGGATCCATA T |
| MS2-11 | 11 | HindIII/Bam HI | ATATAAGCTTCTTTATGGTTTGT*CGTACACC ATCAGGGTACG*GGGATCCATAT |
| MS2Δ-11 | 11 | HindIII/Bam HI | ATATAAGCTTCTTTATGGTTTGT*CGTACCCA TCAGGGTACG*GGGGATCCATAT |
| MS2-12 | 12 | Banm HI/Xba I | ATATGGATCCAAATGTTT*CGTACACCATCAG GGTACG*TTGAACAGTTAATCTAGAATAT |
| MS2Δ-12 | 12 | Bam HI/Xba I | ATATGGATCCAAATGTTT*CGTACCCATCAGG GTACG*TTGAACAGTTAATCTAGAATAT |
| β-cat-3 | 3 | Eco RV/Xho I | ATATGATATCTAGCTATC*AGGCCGATCTATG GACGCTATAGGCACACCGGATACTTTAACGAT TGGCT*GATGTCTATATAGCTATTTTTTTAA CTTCCTTTATTTTCCTTACAGGGTTTCAGAC AAAATCAAAAGAAGGAAGGTGCTCACAT TCCTTAAATTAAGGAGTAAGTCTGCTCGAG ATAT |
| β-catΔ-3 | 3 | Eco RV/Xho I | ATATGATATCTAGCTATC*TCGGTTAGCAATTT CATAGGCCACACGGATATCGCAGGTATCTAGC CGGA*GATGTCTATATAGCTATTTTTTTAAC TTCCTTTATTTTCCTTACAGGGTTTCAGACA AAATCAAAAGAAGGAAGGTGCTCACATTC CTTAAATTAAGGAGTAAGTCTGCTCGAGAT AT |
| β-cat-6 | 6 | Cla I/Xho I | ATATATCGATGTCTATATAGCTATTTTTTTT AACTTCCTTTATTTTCCTTAC*AGGCCGATCTA TGGACGCTATAGGCACACCGGATACTTTAACG ATTGGCTAGG*GTTTCAGACAAAATCAAAA GAAGGAAGGTGCTCACATTCCTTAAATTAA GGAGTAAGTCTGCTCGAGATAT |
| β-catΔ-6 | 6 | Cla I/Xho I | ATATATCGATGTCTATATAGCTATTTTTTTT AACTTCCTTTATTTTCCTTAC*TCGGTTAGCAA TTTCATAGGCCACACGGATATCGCAGGTATCT AGCCGGAAGG*GTTTCAGACAAAATCAAAA GAAGGAAGGTGCTCACATTCCTTAAATTAA GGAGTAAGTCTGCTCGAGATAT |
| NF-κBp50(1)-3 | 3 | Eco RV/Xho I | ATATGATATCTAGCTATC*GCATCCTGAAACT GTTTAAGGTTGGCCGATGC*GATGTCTATATA GCTATTTTTTTTAACTTCCTTTATTTTCCTTA CAGGGTTTCAGACAAAATCAAAAGAAGG AAGGTGCTCACATTCCTTAAATTAAGGAGT AAGTCTGCTCGAGATAT |

-continued

| Name | Restriction Position sites | Cassette (5'-3') |
|---|---|---|
| NF-κBp50(1)Δ-3 | 3 Eco RV/Xho I | ATATGATATCTAGCTATCCGTAGCCGGTTGG<br>AATTTTGTCAAAGTCCTACGGATGTCTATATA<br>GCTATTTTTTTAACTTCCTTTATTTTCCTTA<br>CAGGGTTTCAGACAAAATCAAAAAGAAGG<br>AAGGTGCTCACATTCCTTAAATTAAGGAGT<br>AAGTCTGCTCGAGATAT |
| NF-κBp50(2)-3 | 3 Eco RV/Xho I | ATATGATATCTAGCTATCCGCGCGATCTTGA<br>AACTGTTTTAAGGTTGGCCGATCGCGCGGATG<br>TCTATATAGCTATTTTTTTAACTTCCTTTAT<br>TTTCCTTACAGGGTTTCAGACAAAATCAAA<br>AAGAAGGAAGGTGCTCACATTCCTTAAATT<br>AAGGAGTAAGTCTG CTCGAGATAT |
| NF-κBp65-3 | 3 Eco RV/Xho I | GAAGCTTACAAGAAGGACAGCACGAATAAAAC<br>CTGCGTAAATCCGCCCCATTTGTGTAAGGGTA<br>GTGGGTCGAATTCCGCTCAGATGTCTATATA<br>GCTATTTTTTTAACTTCCTTTATTTTCCTTA<br>CAGGGTTTCAGACAAAATCAAAAAGAAGG<br>AAGGTGCTCACATTCCTTAAATTAAGGAGT<br>AAG |
| NF-κBp65Δ-3 | 3 Eco RV/Xho I | ACTCGCCTTAAGCTGGGTGATGGGAATGTGTT<br>TACCCCGCCTAAATGCGTCCAAAATAAGCACG<br>ACAGGAAGAACATTCGAAGGATGTCTATATA<br>GCTATTTTTTTAACTTCCTTTATTTTCCTTA<br>CAGGGTTTCAGACAAAATCAAAAAGAAGG<br>AAGGTGCTCACATTCCTTAAATTAAGGAGT<br>AAG |

Aptamer and mutant cassette sequences containing portions of the SMN1 mini-gene were digested and ligated into the appropriate restriction sites within the SMN1-GFP plasmid (see the plasmid table above). Briefly, oligonucleotides encoding the forward and reverse strands of the wild-type and mutant MS2 coat protein aptamers were annealed, digested with the appropriate restriction enzymes and ligated into SMN1-GFP. β-catenin aptamer constructs were generated through PCR using the oligonucleotide cassette templates β-cat-3, β-catΔ-3, β-cat-6, and β-catΔ-6 (see aptamer cassette sequence table) and reverse primer AptRv with forward primers Bcat3, BcatΔ3, Bcat6, and BcatΔ6, respectively (see primer sequence table). Similarly, for the NF-κB p50 and p65 aptamer constructs, the oligonucleotide cassette templates NF-κBp50(1)-3, NF-κBp50(1)Δ-3, NF-κBp50(2)-3, NF-κBp65-3, and NF-κBp65Δ-3 were PCR amplified with reverse primer AptRv and forward primers p50(1), p50(1)Δ, p50(2), and p65, respectively. The resulting β-catenin, NF-κB p50 and p65 wild-type and mutant PCR products were digested with the appropriate restriction enzymes and ligated into the corresponding restriction sites of SMN1-GFP (pCS1775-pCS1783, plasmid table).

To construct the multi-input RNA devices containing the wild-type and mutant MS2 coat protein aptamers in positions 3 and 10, the MS2-3 and MS2Δ-3 annealed cassettes were digested with EcoRV and XhoI and ligated into the corresponding restriction sites of SMN1-GFP containing the wild-type and mutant MS2 coat protein aptamers in position 10 (pCS1784-pCS1787, plasmid table). To construct the multi-input RNA devices containing the wild-type and mutant NF-κB p65 aptamers in position 3 and the wild-type and mutant MS2 coat protein aptamers, the NF-κB p65 PCR products were digested with EcoRV and Xho I and ligated into the corresponding restriction sites of SMN1-GFP containing the wild-type and mutant MS2 coat protein aptamers in position 10 (pCS1788-pCS1791, plasmid table).

The SMN1-Puma and SMN1-TK fusion plasmids were constructed in two steps. The human Puma gene was amplified from pORF5-hPUMA (Invivogen) with primers Puma1 and Puma2 designed to place a flexible Gly-Ser linker (GGSGGS) at the 5' end of the gene. The resulting PCR product was digested with NheI and PmeI and ligated into the corresponding restriction sites of pcDNA5/FRT to construct the plasmid pCS1792. The SMN1-GFP constructs pCS1793-pCS1794, pCS1777-pCS1778, pCS1782-pCS1783 were digested with NheI and the resulting SMN1 mini-genes were ligated into the corresponding restriction site in pCS1773, resulting in plasmids MS2-3-Puma, MS2Δ-3-Puma, β-cat-6-Puma, β-catΔ-6-Puma, p65-3-Puma, and p65Δ-3-Puma (pCS1795-pCS1800, plasmid table). Similarly, to construct the SMN1-TK plasmids the HSV-TK gene was amplified from pCD19t-Tk-T2A-IL15op_epHIV7 (a generous gift from M. Jensen, City of Hope) using primers TK1 and TK2. The resulting PCR product was digested with NheI and PmeI and ligated into corresponding restriction sites of pcDNA5/FRT creating pCS1801. The NheI digested SMN1 mini-genes from pCS1777-pCS1778 and pCS1782-pCS1783 were ligated into the corresponding restriction site of pCS1801, resulting in plasmids β-cat-6-TK, β-catΔ-6-TK, p65-3-TK, and p65Δ-3-TK (pCS1802-pCS1805, plasmid table).

To construct the MS2-DsRed expression plasmid (pCS1392), the DsRed monomer gene was amplified from pDsRed-monomer (Clontech) with primers DsRed1 and DsRed2, digested with BamHI and NotI and ligated into the corresponding restriction sites of pcDNA5/FRT creating pCS489. The MS2 coat protein gene was amplified in two steps from template pHis-BIVT-MS2-RSp55 (Graveley et al., Embo J 17, 6747, 1998) using primers MS2-1 and MS2-2 for the first round and MS2-3 and MS2-2 for the second round to fuse a FLAG epitope (DYKDDDDK) (Chubet and Brizzard, Biotechniques 20, 136, 1996) followed by an SV40 NLS (PKKKRKV) (Kalderon et al., Cell 39, 499, 1984), to the 5' end of the MS2 coat protein gene. The final PCR product was digested with KpnI and BamHI and ligated into the corresponding restriction sites of pCS489. The p50-DsRed expression plasmid (pCS1806) was constructed similarly, where the p50 gene was amplified in two steps from template pGAD424 (Cassiday and Maher, 3rd, *Proc Natl Acad Sci USA* 100, 3930, 2003) using primers p50-1 and p50-2 for the first round and p50-3 and p50-2 for the second round to fuse a FLAG epitope followed by a SV40 NLS to the 5' end of the p50 gene. The final PCR product was digested with NheI and KpnI and ligated into the corresponding restriction sites pCS489.

Figure 9A:
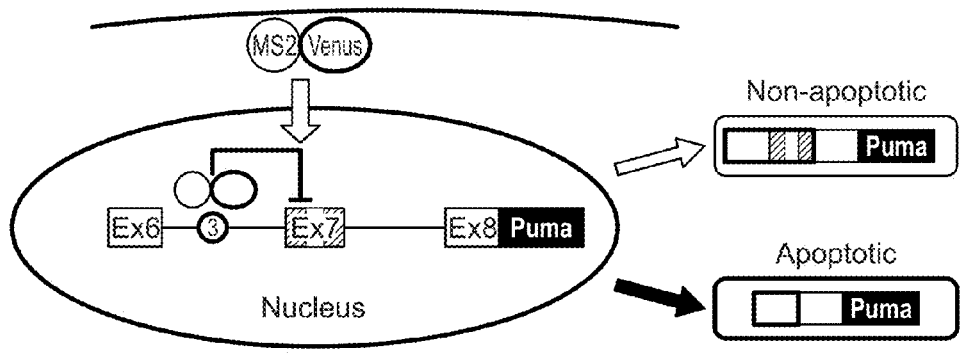
FIG. 9A shows a mechanism of the MS2-responsive device fused to an output module that results in apoptosis (Puma). See Buskirk and Liu, *Chem Biol* 12, 151, 2005 (GFP coding sequence was replaced with the proapoptotic gene Puma, where the overexpression of Puma induces rapid apoptosis).
Figure 9B:
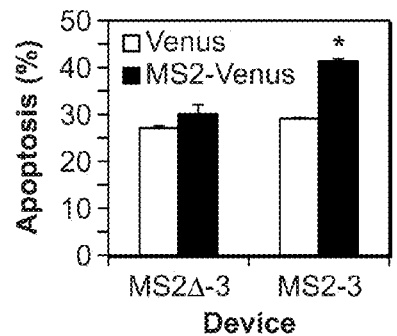
FIG. 9B shows that the MS2-responsive (MS2-3) device fused to Puma triggers increased levels of apoptosis in cells heterologously expressing the MS2-Venus fusion protein. Apoptosis of the wild-type and mutant devices was assessed by flow cytometry in the presence of the MS2-Venus fusion and Venus. For all reported activities, the mean cell survival and apoptosis levels from two independent experiments are shown. Cells stably expressing the MS2 device (MS2-3) linked to Puma displayed a 50% increase in apoptosis in the presence of a MS2-Venus (fluorescent protein) fusion construct compared to cells transfected with Venus alone, whereas the mutant MS2 device resulted in an insignificant response (~10%).
Figure 9C:
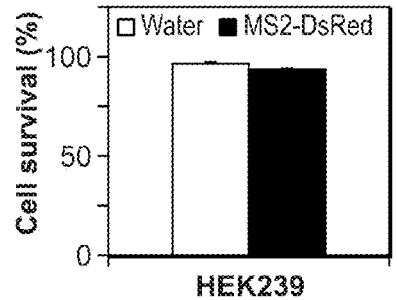
FIG. 9C shows flow cytometry analysis of cell survival percentages of HEK293 cells alone and in the presence of MS2-DsRed. The results demonstrate that HEK293 cells have a high level of cell viability that is not affected by transient transfection.
Figure 9D:
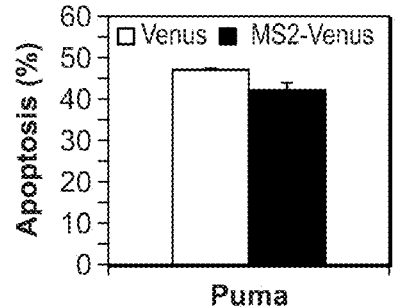
FIG. 9D shows flow cytometry analysis of apoptosis in HEK293 cells stably expressing Puma alone. Apoptosis of this cell line was assessed in the presence of the MS2-Venus fusion and Venus alone.
Figure 9E:
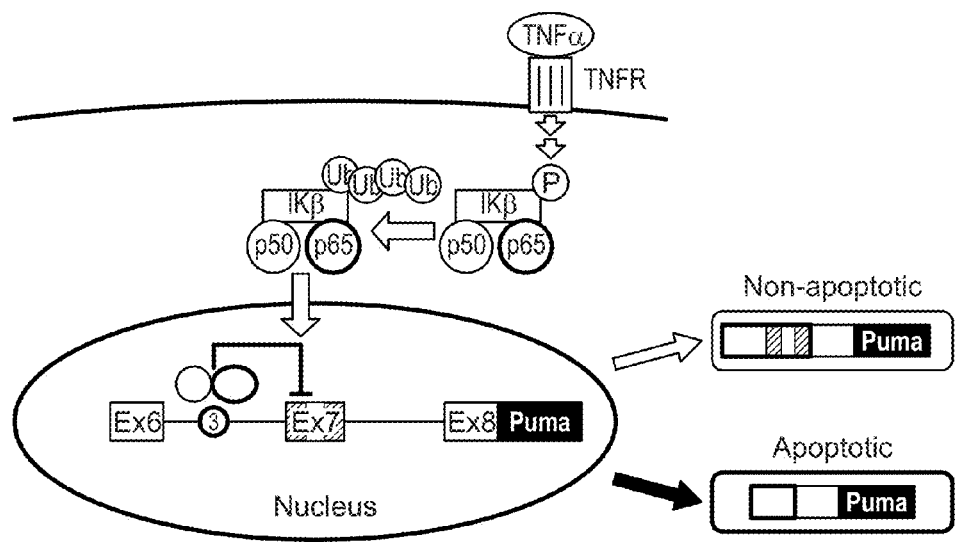
FIGS. 9E and 9F show mechanisms of the β-catenin- and NF-κB-responsive devices fused to the apoptosis output module (Puma), which trigger apoptosis in response to detection of disease markers. The β-catenin-(β-cat-6) and NF-κB p65-responsive (p65-3) devices fused to Puma trigger increased levels of apoptosis in cells where signaling has been stimulated through these pathways. Stimulation of the β-catenin pathway led to a significant ~2-fold increase in apoptosis in cells stably expressing the β-cat-6 device (P<0.01). Cells stably expressing the p65-3 devices exhibited a 40% increase in apoptosis in response to TNF-α (P<0.05). Apoptosis was assessed by flow cytometry in the presence and absence of the appropriate stimulation molecule (TNF-α or LTD$_4$).
Figure 9E:
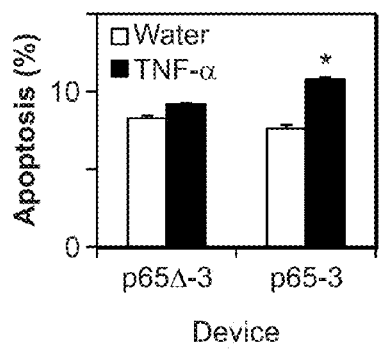
Figure 9F:
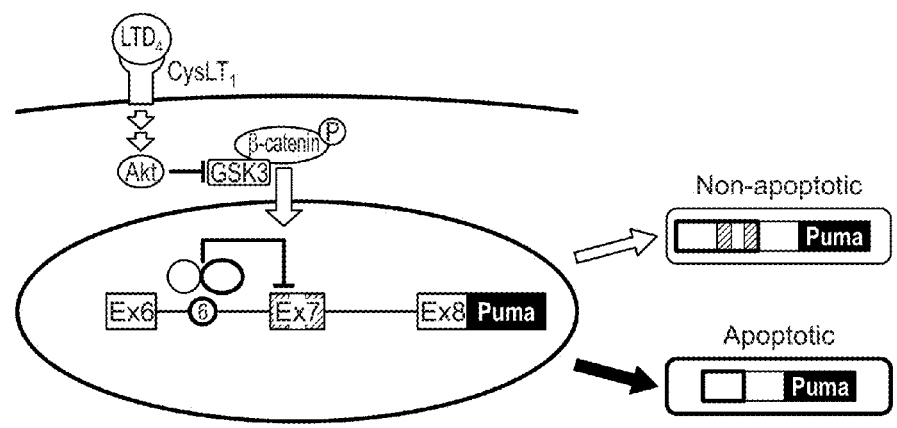
Figure 9F:
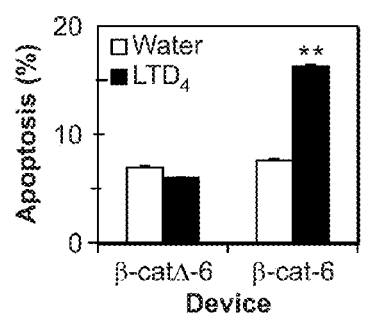

To construct the MS2-Venus expression plasmid (pCS1806), the construct pCS2/Venus (Nagai et al., *Nat Biotechnol* 20, 87, 2002) was digested with BamHI and ApaI and the resulting venus gene was ligated into the corresponding restriction sites of pcDNA5/FRT creating pCS1807. pCS1392 was digested with KpnI and BamHI and the resulting FLAG-NLS-MS2 fragment was ligated into the corresponding restriction sites of pCS1807. Venus was chosen as our fluorescent reporter for the MS2 induced apoptosis studies (FIGS. 9A and 9B) to avoid significant spectral overlap with the 7-aminoactinomycin D (7AAD) viability dye.

Example 2

Regulation of Alternative Splicing by Altering Aptamer Integration Positions in the Protein-Responsive RNA-Based Regulatory Devices While not wishing to be bound by any particular theory, it is contemplated that the recruitment of proteins to a transcript through binding to an integrated aptamer sequence can alter splicing patterns through at least two different mechanisms. First, the recruited protein can hinder the binding of other trans-acting splicing factors or spliceosomal components. For example, by hindering the binding of enhancers or spliceosomal components, protein binding would result in increased exon exclusion, whereas by hindering the binding of silencers, it would result in increased inclusion. Second, the recruited protein may in turn act to recruit other splicing factors to the transcript through protein-protein interactions between the protein ligand and the splicing factor. The resulting splicing pattern may depend on whether an enhancer or silencer is recruited to the transcript. Therefore, the resulting effect of protein binding to the aptamer may be a function of the relative location in the transcript (i.e., aptamer location relative to other cis-acting splicing regulatory sequences) and the identity of the protein (i.e., any protein-protein interaction domains that may allow the protein to recruit other factors that may in turn affect splicing).

For example, position-dependent effects of aptamer integration can be effected by the relative distances of the sites from cis-acting splicing sequences. Positions located at (or near) critical distances from important splicing elements, such as the 5' splice site, the branch point, and the 3' splice site, may have stronger influence on alternative splicing. In addition, different protein-specific and ligand binding properties may be used to exert different effects on alternative splicing, even for identical aptamer integration positions. Therefore, increased exon exclusion may result from steric hindrance of an enhancer or spliceosomal component that bind to the aptamer-bound protein ligand, whereas increased exon inclusion may result via interacting with and recruiting a splicing factor that acts to enhance splicing.

This example demonstrates that both mechanistic models described above may be employed to affect alternative splicing by altering the aptamer integration locations and/or by using different protein ligands.

Figure 5A:
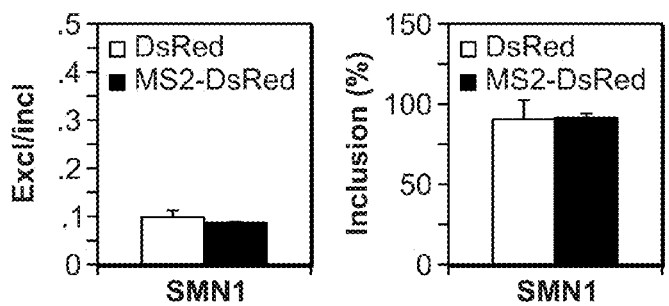
FIG. 5A shows transcript isoform analysis of the SMN1-GFP construct (which harbors a natural stop codon in the alternatively spliced exon) lacking an aptamer input module with primer sets specific for exon 7 excluded and included products demonstrates that the presence of the MS2-DsRed fusion protein does not alter splicing patterns. For all qRT-PCR data, expression levels of duplicate samples were normalized to the levels of HPRT. Data is reported as the ratio of the mean expression levels of the exon 7 excluded isoform to the exon 7 included isoform±the average error. Exon inclusion percentages are shown. All error bars represent +/−s.d. from the mean values determined from two independent experiments.
Figure 5B:
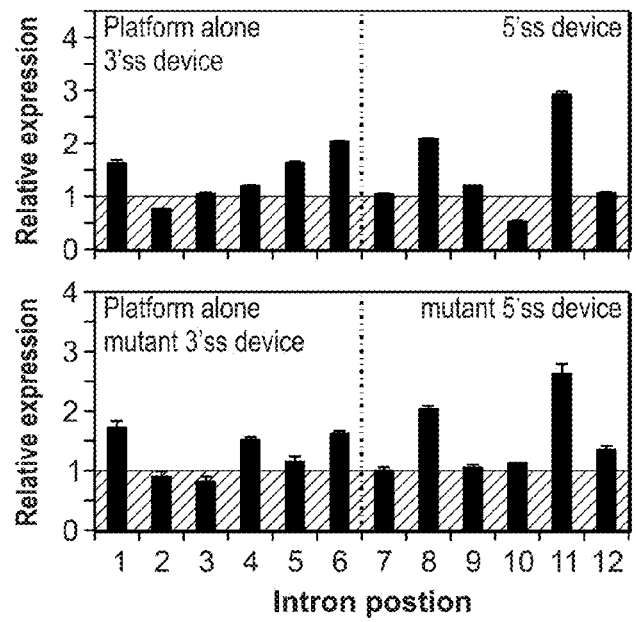
FIG. 5B shows that the integration of the wild-type and mutant aptamer input modules can affect the regulatory output of the device. The observed effects are consistent between those observed from the wild-type (upper panel) and mutant (lower panel) aptamer input modules in the absence of ligand. Activities are reported as relative expression by taking the ratio of the mean GFP levels of the indicated RNA device to that from the SMN1-GFP construct lacking an aptamer input module as determined from flow cytometry analysis. For all reported activities, expression levels were determined by flow cytometry analysis from two independent experiments.
Figure 5C:
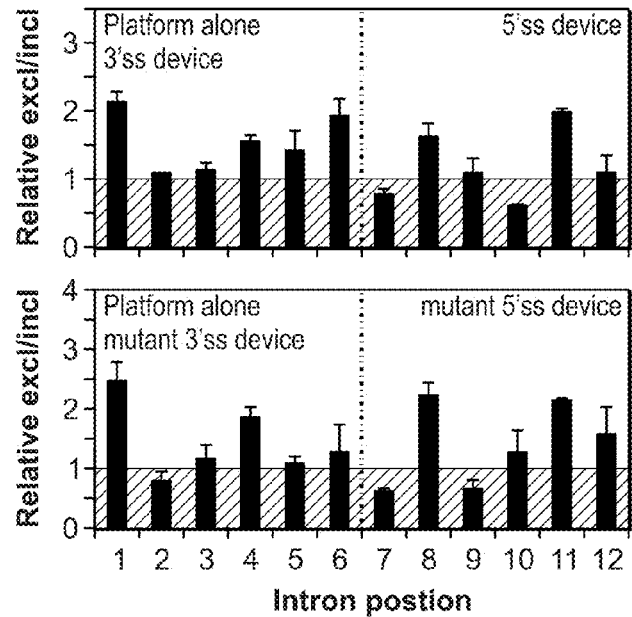
FIG. 5C shows transcript isoform analysis of the wild-type (upper panel) and mutant (lower panel) MS2-responsive devices. qRT-PCR data supports gene expression data (FIG. 5B). Data is reported as the ratio of the mean expression levels of the exon 7 excluded isoform to the exon 7 included isoform for the wild-type and mutant devices relative to the same ratio for the SMN1-GFP construct lacking an aptamer input module.

Six subject devices were constructed by inserting the aptamer for the bacteriophage coat protein MS2 (Carey et al., *Biochemistry* 22, 4723, 1983) at 6 different positions in each intron (1-12) of the SMN1 mini-gene (Culler et al., *Nucleic Acids Res*, 38, 5152, 2010) (FIG. 1C and FIG. 5A), and linked the device to the gene encoding green fluorescent protein (GFP). The SMN1 mini-gene has its key regulatory sequences located in exon regions (Cartegni et al., *Am J Hum Genet* 78, 63, 2006), and insertion of synthetic sequences into its intronic regions is not likely to strongly affect splicing patterns. Human embryonic kidney (HEK)-293 cell lines that stably expressed these devices or the corresponding negative controls expressing mutant aptamers (see Example 1) displayed differences in fluorescence compared to cells expressing a device containing no aptamer sequence, with insertion at most positions causing increased exon exclusion (FIGS. 5B and 5C), indicating that secondary structure can modulate splicing patterns.

Figure 1C:
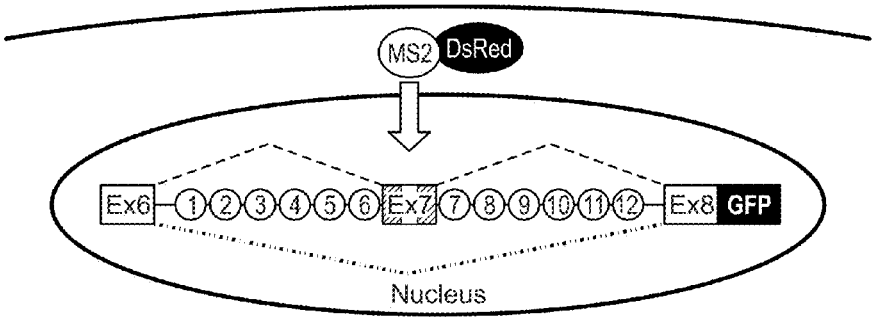
FIG. 1C illustrates means for determining optimal input module location within intronic sequence space of the regulatory device. The MS2 aptamer was inserted at 12 intronic positions spaced by 15-nts flanking the alternatively spliced exon.
Figure 1D:
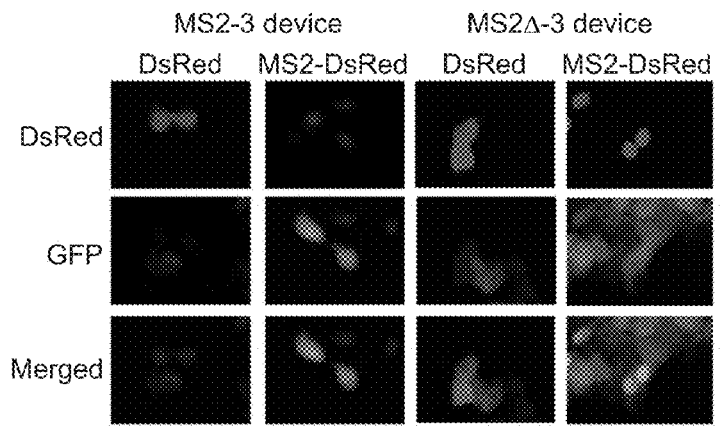
FIG. 1D shows fluorescence images of the MS2-responsive devices. The increased fluorescence output from an MS2-responsive device is specific to the MS2-DsRed protein input (compared to DsRed alone) and the wild-type MS2 aptamer in position 3 (MS2-3) (compared to loss-of-function mutant MS2 aptamer MS2Δ-3).
Figure 1E:
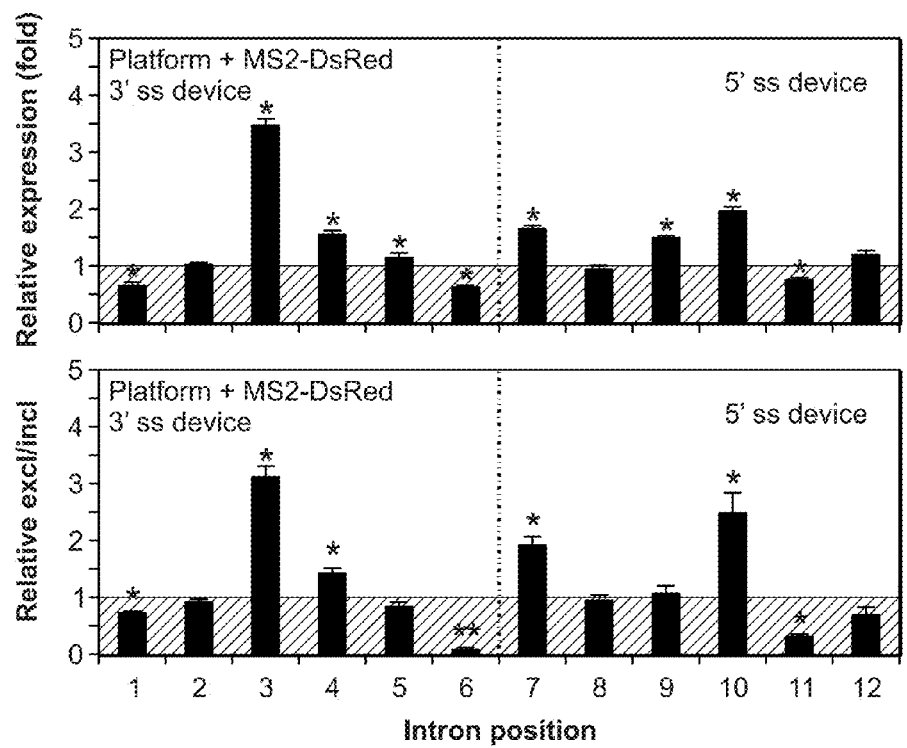
FIG. 1E shows that the response of the MS2-responsive device to the MS2-DsRed protein is affected by the location of the input module. For all activities reported as relative expression (fold), the ratio of the mean GFP levels of the wild-type RNA device in the presence of ligand (MS2-DsRed) to the absence of ligand (DsRed) is normalized to the same ratio for the mutant device. Transcript isoform analysis of the MS2-responsive devices with qRT-PCR supported the gene expression data (bottom panel). For all qRT-PCR data reported as relative excl/incl (fold), the ratio of the mean expression levels of the exon 7 excluded isoform to the exon 7 included isoform for the wild-type device in the presence of ligand to the absence of ligand is normalized to the same ratio for the mutant device. For all reported activities, mean expression levels from two independent experiments are shown. Error bars represent +/−s.d. from mean values. P-values derived from the Student's t-test are as follows: *P<0.05 and **P<0.01. Unnormalized expression levels for all devices are available but not provided herewith.
Figure 5D:
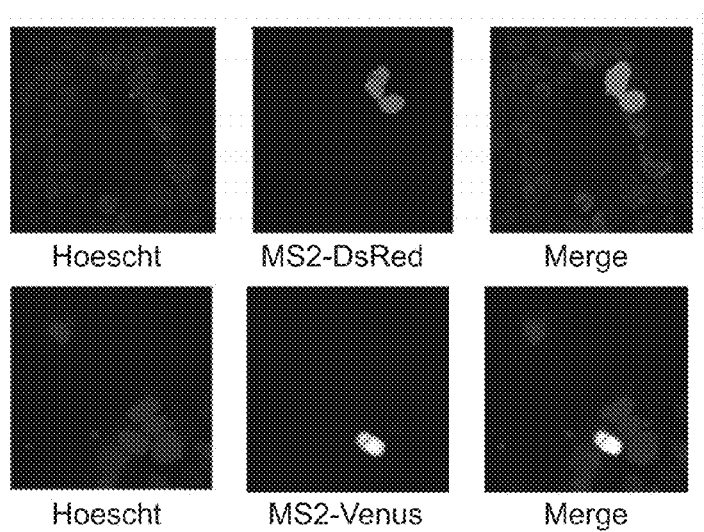
FIG. 5D shows confocal images of HEK293 Flp-In cells expressing the MS2-DsRed and MS2-Venus fusion constructs. The MS2-DsRed and MS2-Venus fusion proteins colocalize with the Hoescht nuclear stain in cells transiently expressing the constructs.
Figure 5E:
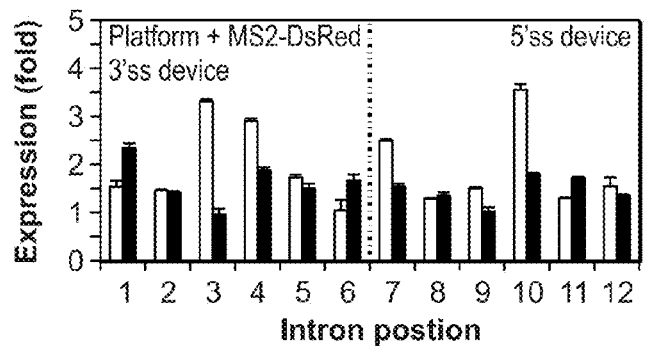
FIG. 5E shows that the response of the MS2-responsive device to heterologously expressed MS2-DsRed fusion protein is affected by the location of the input module and demonstrates specificity of device response to the wild-type aptamer. Activities for the wild-type (light gray bars) and mutant devices (dark gray bars) are reported as expression (fold), where the ratio of the mean GFP level of the device in the presence of MS2-DsRed (presence of ligand) is normalized to the mean GFP level in the presence of DsRed alone (absence of ligand).
Figure 5F:
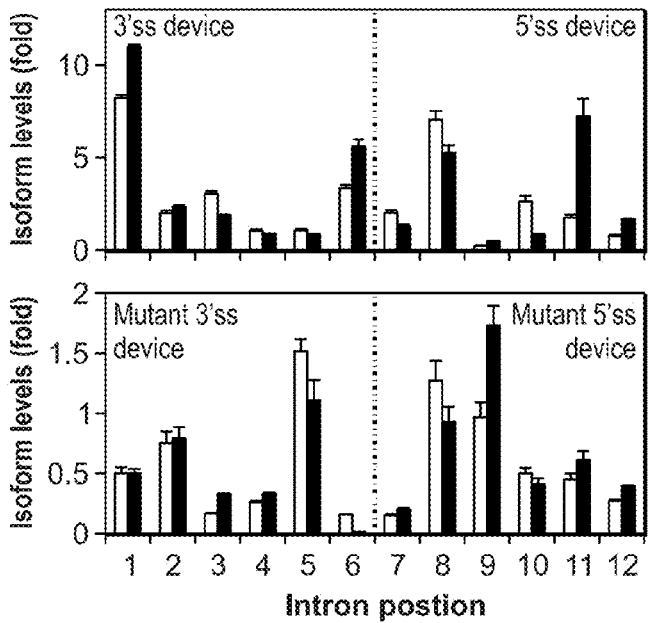
FIG. 5F shows transcript isoform analysis of the wild-type (upper panel) and mutant (lower panel) MS2-responsive devices with primer sets specific for exon 7 excluded (light gray bars) and included (dark gray bars) products. Transcript isoform levels are reported as isoform levels (fold), where the mean isoform level in the presence of MS2-DsRed (presence of ligand) is normalized to the mean isoform level in the presence of DsRed alone (absence of ligand) ±the average error.

To examine protein-specific effects on splicing, cell lines were transfected with a plasmid encoding the MS2 coat protein fused to fluorescent protein DsRed and a Simian virus 40 (SV40) nuclear localization signal (MS2-DsRed) (FIG. 1C and FIG. 5D). Integration of aptamers into 6 positions resulted in increases in fluorescence ($P<0.05$, Student's t-test) and 3 positions resulted in decreases in fluorescence ($P<0.05$) relative to that of cell lines expressing DsRed. Control experiments showed that these effects were specific to the wild-type aptamer (FIGS. 1D and 1E, FIG. 5E). Transcript isoform analysis by quantitative real-time polymerase chain reaction (qRT-PCR) confirmed the effect on splicing (FIG. 1E and FIG. 5F), and there was a significant correlation between splicing patterns and fluorescence ($P<<0.01$, Anova). Although the regulatory effects of the devices were modest (~2- to 4-fold), these effects are comparable to those in other splicing (Kim et al., *BMC Mol Biol* 9, 23, 2008) and RNA regulatory (Arndt et al., *BMC Cancer* 9, 374, 2009) systems that have key roles in controlling biological processes.

Three representative integration locations, positions 3, 6, and 10, were selected as points of input module integration for device tailoring on the basis of their relative amount of protein-mediated splicing regulation and location relative to splicing motifs (e.g., 3' ss, 5' ss, branch point, and polypyrimidine tract).

Example 3

Modularity of the Input Processing Function—NF-κB Pathway

This example demonstrates the modularity of the input processing function of the subject RNA devices and their ability to detect nuclear localized proteins resulting from activated signaling pathways.

Figure 2A:
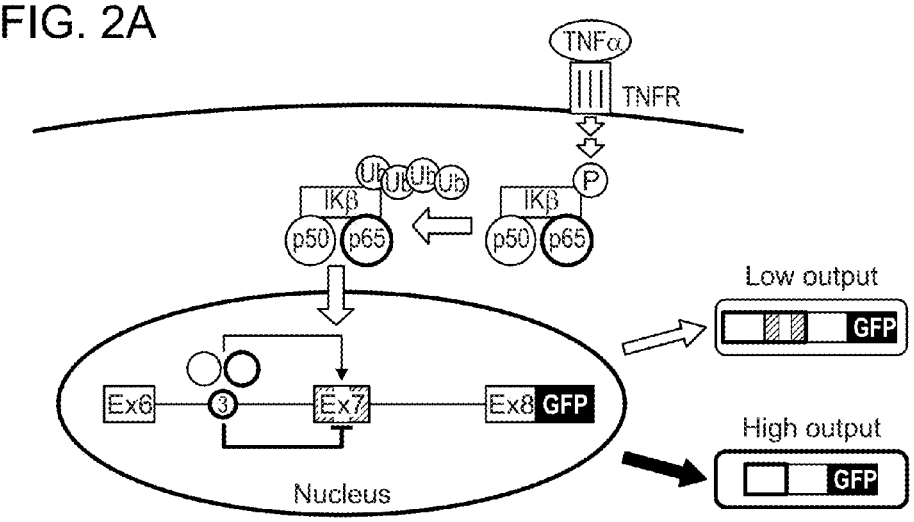
FIG. 2A illustrates the mechanism of the NF-κB-responsive device based on TNF-α stimulation (20 ng/ml) of the NF-κB pathway. Ligand binding to the TNF-α receptor leads to activated signaling and translocation of p50 and p65 into the nucleus. The NF-κB-responsive devices contain NF-κB p65 (p65-3) or p50 (p50(1)-3 and p50(2)-3) aptamers inserted into position 3.
Figure 2B:
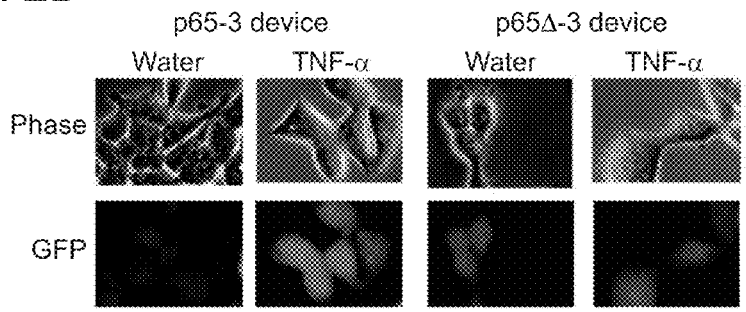
FIG. 2B shows phase (top) and fluorescence (bottom) images of the NF-κB p65-responsive devices. The increased fluorescence output from a NF-κB-responsive device is specific to the pathway stimulation and the wild-type p65 aptamer in position 3 (p65-3).
Figure 2C:
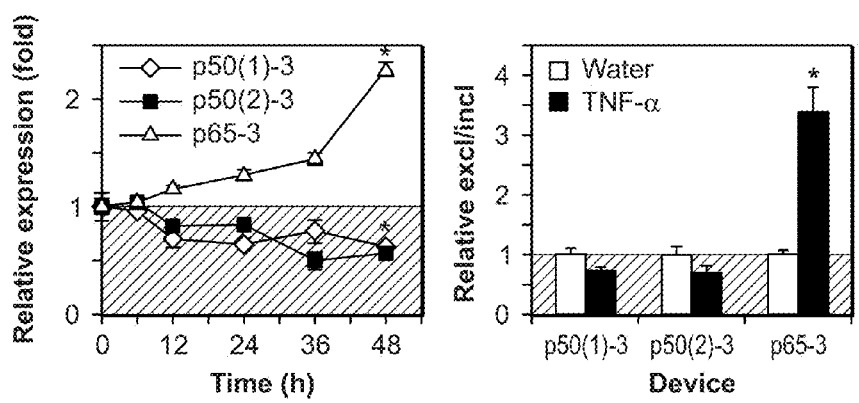
FIG. 2C shows that NF-κB-responsive devices exhibited responses to TNF-α stimulation at the level of gene expression (left panel) and splicing pattern (right panel). For all data, relative expression (fold) was determined as described in FIG. 1F. qRT-PCR data is reported as relative excl/incl, the ratio of the mean expression levels of the exon 7 excluded isoform to the exon 7 included isoform for the wild-type device relative to the same ratio for the mutant device under the indicated ligand condition.
Figure 2D:
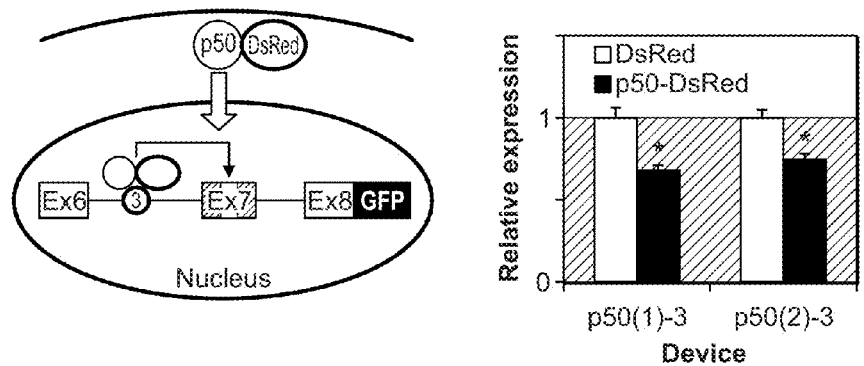
FIG. 2D shows potential mechanism of the NF-κB p50-responsive device based on a p50-DsRed protein input and corresponding device response. The NF-κB p50-responsive devices exhibited responses to a heterologous p50-DsRed protein similar to that observed with TNF-α stimulation. Activities were reported as relative expression by taking the ratio of the mean GFP levels of the wild-type RNA device to that from the mutant device under the indicated ligand condition.
Figure 6A:
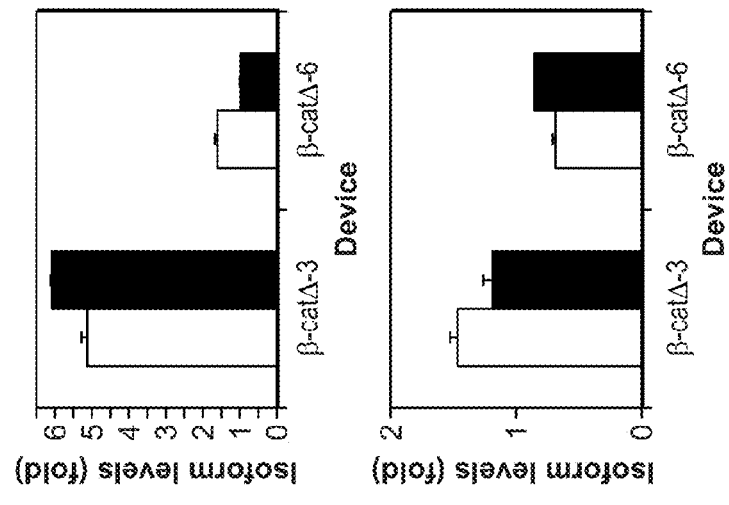
FIG. 6A shows transcript isoform analysis of the wild-type (upper panel) and mutant (lower panel) NF-κB-responsive devices with primer sets specific for exon 7 excluded (light gray bars) and included (dark gray bars) products. Transcript isoform levels are reported as isoform levels (fold), where the mean isoform level in the presence of TNF-α (presence of ligand) is normalized to the mean isoform level in the presence of water alone (absence of ligand) ±the average error.
Figure 6B:
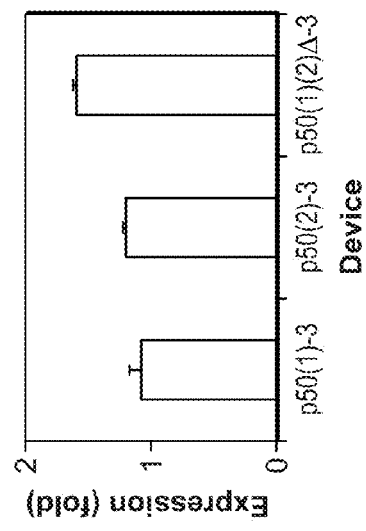
FIG. 6B shows that the NF-κB p50-responsive devices exhibit responses to a heterologously expressed p50-DsRed fusion protein similar to that observed with TNF-α stimulation. Activities for the wild-type and mutant NF-κB p50-responsive devices are reported as expression (fold), where the mean GFP level of the device in the presence of p50-DsRed (presence of ligand) is normalized to the mean GFP level in the presence of DsRed alone (absence of ligand).

To this end, devices were built with aptamers that bind the subunits p50 (Mi et al., *Nucleic Acids Res* 34, 3577, 2006; Chan et al., *Nucleic Acids Res* 34, e36, 2006) and p65 (Wurster and Maher, 3rd, *Rna* 14, 1037, 2008) of the transcription factor NF-κB inserted into position 3 (FIG. 2A). NF-κB p50 and p65 dimers have an important role in disease by binding to κB sites in promoters or enhancers of genes participating in immune and inflammatory responses, cell adhesion, proliferation, and apoptosis (Wurster and Maher, 3rd, *Rna* 14, 1037, 2008). NF-κB signaling and subsequent translocation of p50 and p65 to the nucleus was induced in cell lines stably expressing the NF-κB devices with tumor necrosis factor alpha (TNF-α) (Hellweg et al., *Ann N Y Acad Sci* 1091, 191, 2006). The p65-3 device displayed increased gene expression (P<0.01), corresponding to an increase in exon exclusion as a result of p65 binding to the sensor, whereas the p50-3 devices exhibited decreased gene expression (P<0.05) and exon exclusion as a result of p50 binding to the sensor (FIGS. 2B, 2C, & 6A). Controls with mutant aptamer devices showed that responses were specific to the wild-type aptamer sequences. Cell lines expressing the p50-responsive devices and a p50-DsRed fusion exhibited decreases in fluorescence when compared to cells expressing DsRed (FIGS. 2D & 6B), supporting that the response observed under TNF-α stimulation is directly mediated by p50 binding.

The differing output signals from the p65- and p50-responsive devices may be due to differences in aptamer binding (Wurster and Maher, 3rd, *Rna* 14, 1037, 2008), aptamer structure, or interactions of p65 and p50 with spliceosomal components. Specifically, these two proteins have contrasting structural domains that mediate protein-protein interactions, where p65 has a trans-activation domain and p50 has a trans-repression domain (Jiang et al., *Biochem Biophys Res Commun* 301, 583, 2003). In addition, the affinities of both aptamers for their cognate ligand differ by 2-fold (Wurster and Maher, 3rd, *Rna* 14, 1037, 2008; Huang et al., *Proc Natl Acad Sci USA* 100, 9268, 2003), and the overall conformation and size of the protein dimers bound to the RNA aptamers are different.

Example 4

Modularity of the Input Processing Function—Wnt Pathway

Figure 2E:
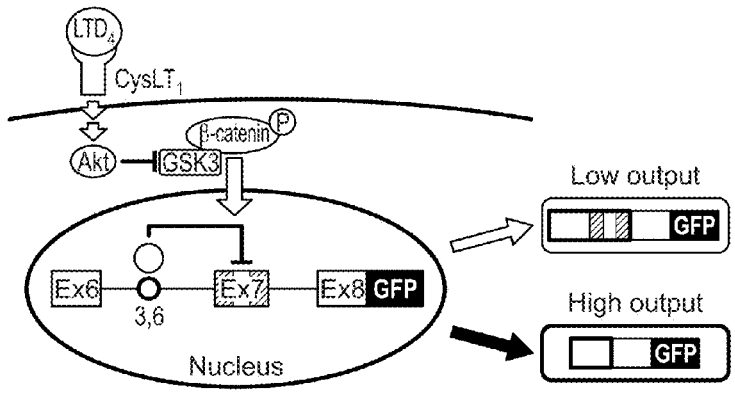
FIG. 2E shows potential mechanism of the β-catenin-responsive device based on LTD$_4$ stimulation (80 nM) of the Wnt pathway. LTD$_4$ stimulation leads to stabilization of β-catenin and accumulation in the nucleus. The β-catenin-responsive devices contain the β-catenin aptamer in positions 3 (β-cat-3) and 6 (β-cat-6).
Figure 2F:
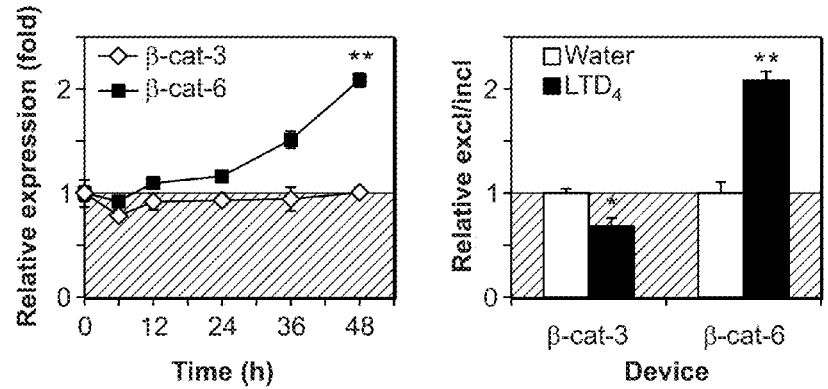
FIG. 2F shows that β-catenin-responsive devices exhibited responses to LTD$_4$ stimulation at the level of gene expression (left panel) and splicing pattern (right panel).
Figure 6C:
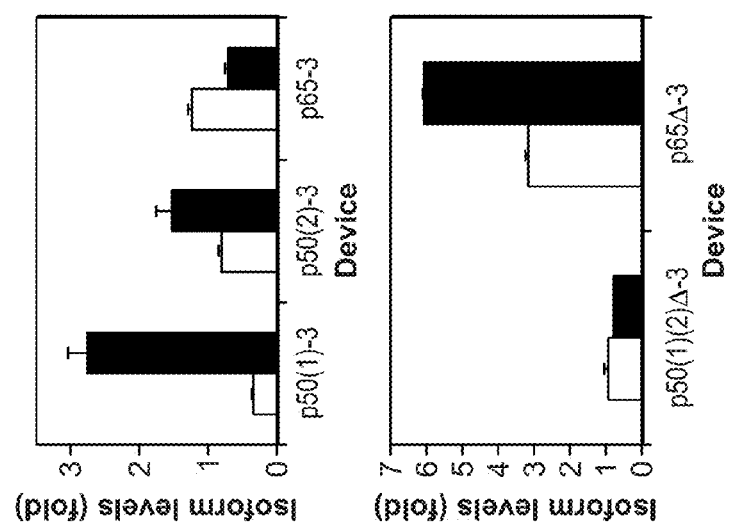
FIG. 6C shows transcript isoform analysis of the wild-type (upper panel) and mutant (lower panel) β-catenin-responsive devices with primer sets specific for exon 7 excluded (light gray bars) and included (dark gray bars) products. Transcript isoform levels are reported as isoform levels (fold), where the mean isoform level in the presence of $LTD_4$ (presence of ligand) is normalized to the mean isoform level in the presence of water alone (absence of ligand) ±the average error.

In another example, aptamers that recognize the signaling protein β-catenin (Lee et al., *Cancer Res* 67, 9315, 2007) were inserted into sites 3 and 6 to build β-catenin-responsive devices (FIG. 2E). β-catenin is a central component of the Wnt signaling pathway and is localized to the nucleus upon pathway activation to aid in the transcription of genes that regulate cell growth, differentiation, and tumorigenesis (Lee et al., *Cancer Res* 67, 9315, 2007). The effect of stimulating the β-catenin pathway on the response of the engineered β-catenin-responsive devices was demonstrated with leukotriene $D_4$ ($LTD_4$). The β-cat-6 device exhibited increased gene expression (P<0.05), corresponding to an increase in exon exclusion (FIGS. 2F & 6C), whereas the β-cat-3 device did not respond to $LTD_4$ stimulation in a significant manner. Control experiments demonstrated that the β-cat-6 device response was specific to the wild-type aptamer sequences.

Results from the MS2, NF-κB, and β-catenin studies demonstrate that particular protein ligands may be used to effect distinct positional as well as functional effects on splicing, such that aptamer position and the target protein provide device tuning capability. These studies verify the flexibility of the subject synthetic devices to be interfaced with cellular signaling pathways, and their ability to detect disease biomarkers and link this detection to regulated gene expression events.

Example 5

Multi-Input Processing Function

Figure 3A:
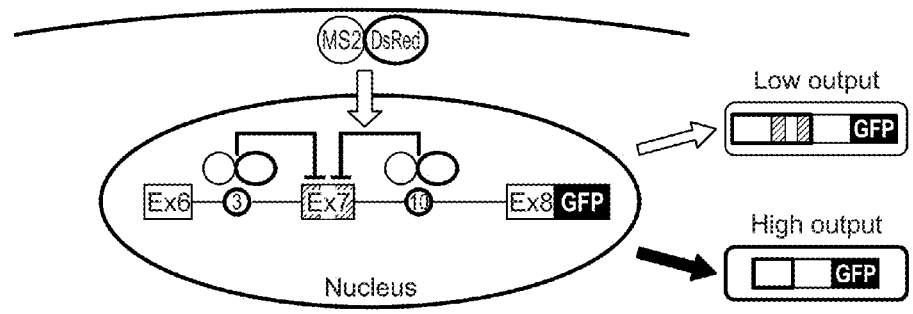
FIG. 3A shows a potential mechanism of the MS2 multi-input processing regulatory device. Wild-type and mutant MS2 aptamers were inserted into positions 3 and 10.
Figure 3B:
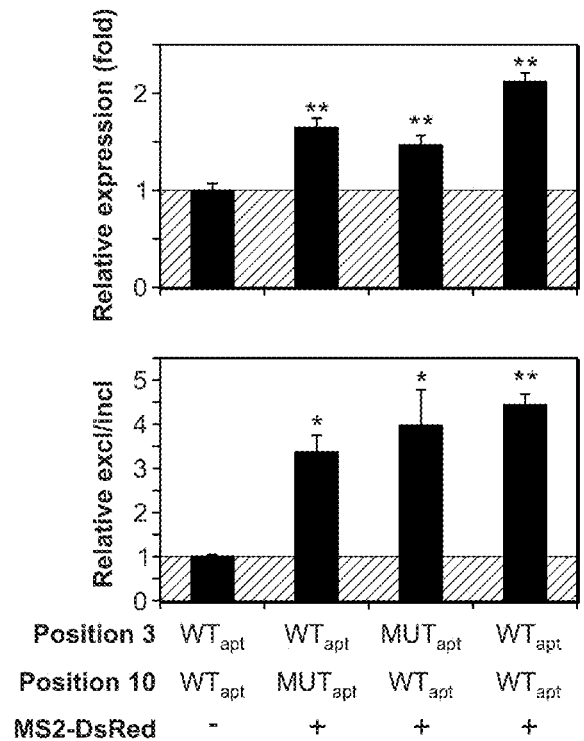
FIG. 3B shows that the MS2 multi-input processing device responds to the heterologous MS2-DsRed protein to increase the gene expression output (top panel). Transcript isoform analysis of the MS2 multi-input processing device supports gene expression data (bottom panel). For all data, relative expression (fold) and relative ratios of exon excluded to included transcript isoforms (fold) were determined as described in FIG. 1F.
Figure 7A:
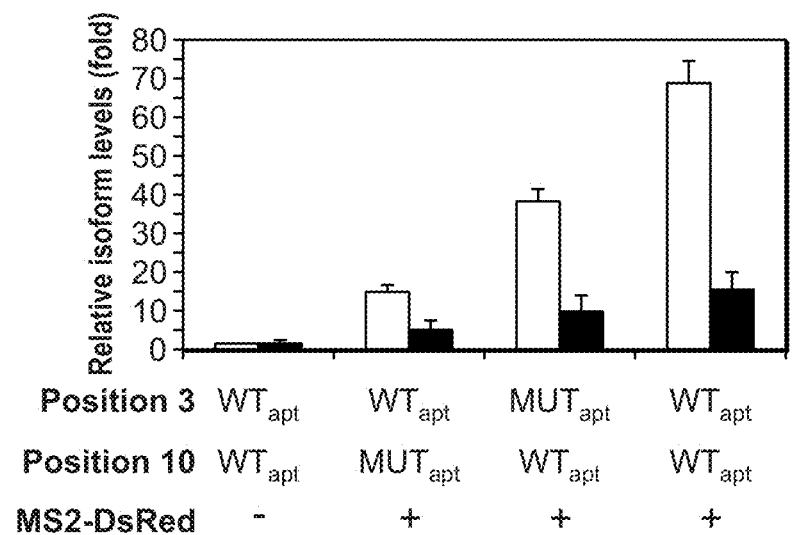
FIG. 7A shows transcript isoform analysis of the MS2 multi-input processing regulatory devices with primer sets specific for exon 7 excluded (light gray bars) and included (dark gray bars) products. Relative isoform levels (fold) are reported by dividing the mean isoform level in the presence of MS2-DsRed (presence of ligand) by the mean isoform level observed with DsRed alone (absence of ligand) ±the average error, where this ratio is normalized by the corresponding ratio for the double mutant control device. Transcript isoform analysis of the MS2 multi-input processing devices also supports gene expression data.

To demonstrate the applicability of the subject device platform for multi-input processing, devices containing combinations of the wild-type and mutant MS2 aptamers in positions 3 and 10 were constructed (FIG. 3A). Devices containing the wild-type aptamer in either position displayed significant increases in gene expression (P<0.01) and exon exclusion in the presence of MS2-DsRed compared to that in the absence of ligand (FIGS. 3B & 7A). A device with aptamers in both positions showed a ~30-45% increase in gene expression and exon exclusion compared to that of the single-aptamer devices.

Figure 3C:
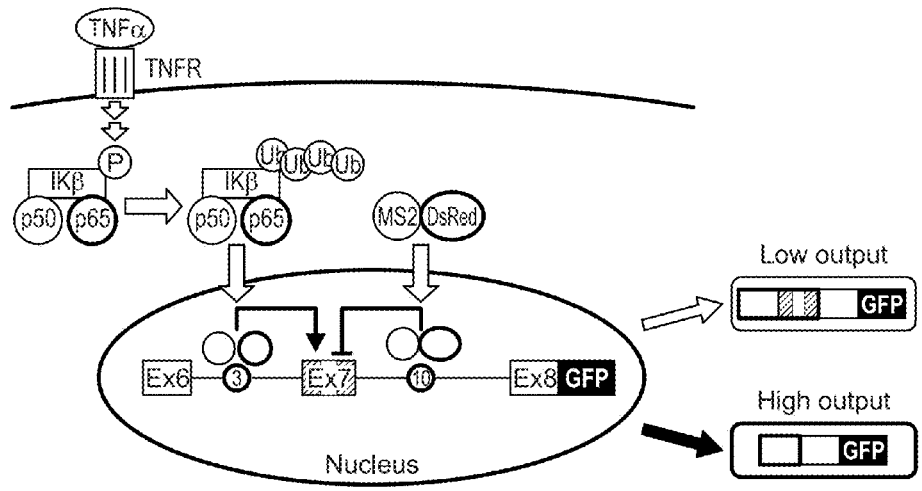
FIG. 3C shows that the MS2/NF-κB p50 multi-input processing regulatory device allows integration of complex input signals and amplification of device response. The NF-κB p50 and MS2 aptamers were inserted into positions 3 and 10, respectively.
Figure 3D:
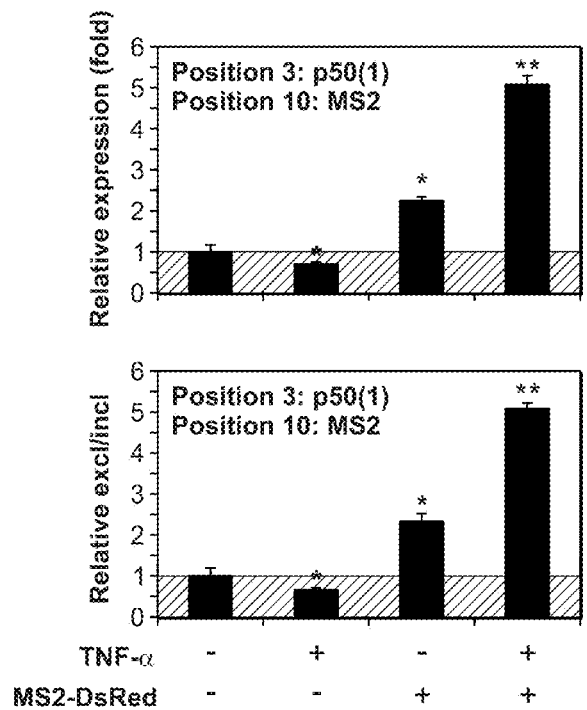
FIG. 3D shows that the MS2/NF-κB p50 multi-input processing device responds to both inputs to increase the gene expression output (top panel). Transcript isoform analysis of the MS2/NF-κB p50 multi-input processing device supports gene expression data (bottom panel).
Figure 7C:
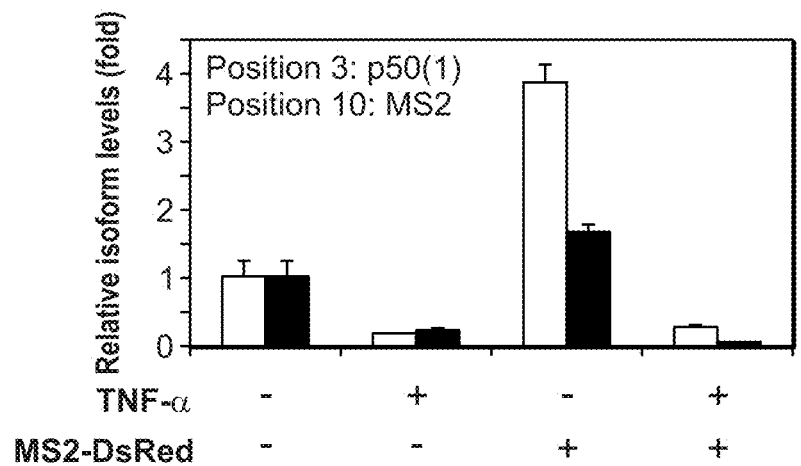
FIG. 7C shows transcript isoform analysis of the MS2/NF-κB p50 multi-input processing devices with primer sets specific for exon 7 excluded (light gray bars) and included (dark gray bars) products.
Figure 7B:
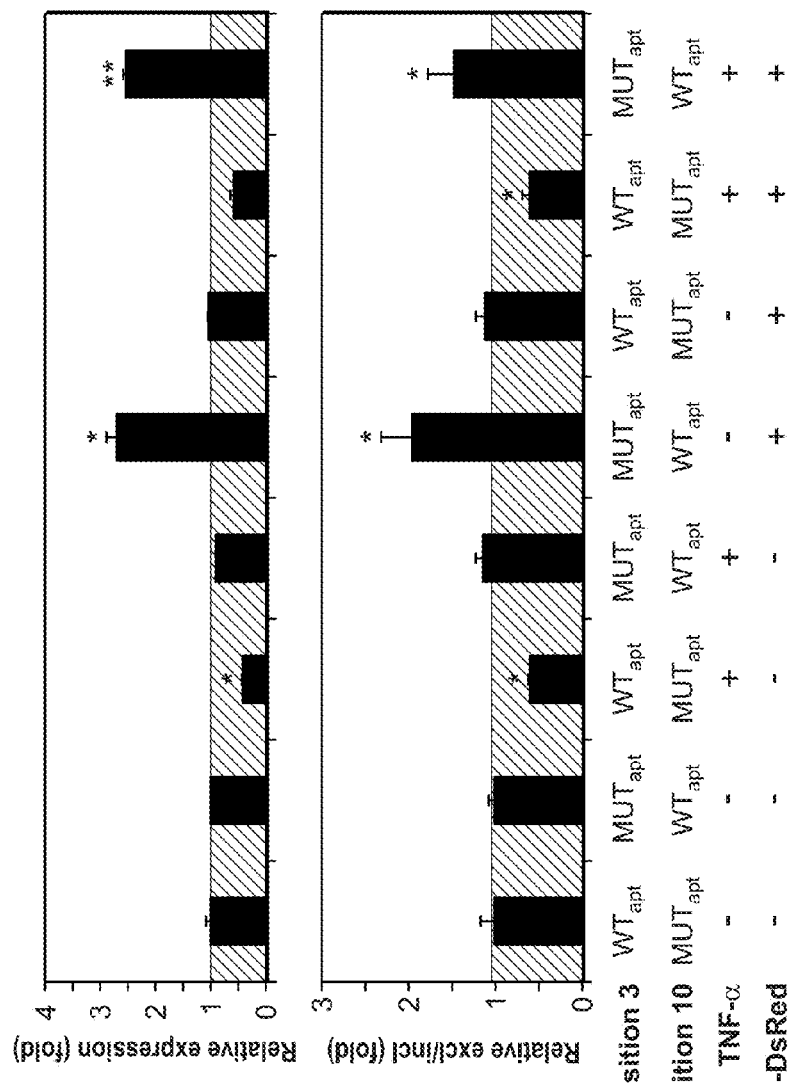
FIG. 7B shows that the MS2/NF-κB p50 multi-input processing device response is specific for the MS2 and NF-κB p50 ligands. Combinations of the NF-κB p50 and MS2 aptamers (wild-type and mutant) were inserted into positions 3 and 10, respectively. P-values derived from the Student's t-test for all reported activities are as follows: *$P<0.05$ and **$P<0.01$. Relative expression (fold) and relative excl/incl (fold) were determined as described in FIG. 1E.

Multi-input devices were also built to detect heterologous MS2-DsRed and endogenous NF-κB p50 (FIG. 3C). Specifically, the wild-type and mutant p50(1) and MS2 aptamers were inserted into sites 3 and 10, respectively. TNF-α stimulation led to a decrease in gene expression and exon exclusion, whereas expression of MS2-DsRed led to a significant increase in gene expression (P<0.05) and exon exclusion from this device (FIGS. 3D, 7B, & 7C). Notably, the device response in the presence of both ligands was greater than the sum of the individual ligand output signals, suggesting that the combined inputs have a synergistic effect on the output signal. These studies indicate that the subject device platform can support combinatorial regulation of gene expression in response to multiple protein inputs.

Example 6

Regulation of Cell-Fate Decision

Figure 4A:
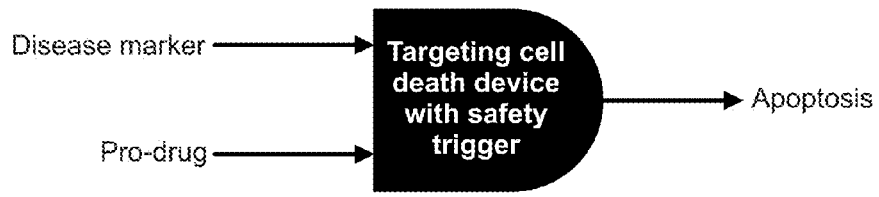
FIG. 4A is a functional representation of a targeted therapeutic device that integrates across two therapeutic inputs—disease biomarker and an exogenously-applied, inactive pro-drug—to trigger targeted cell death.

To demonstrate that the subject protein-responsive RNA devices can be used to regulate cell-fate decisions, devices were developed to integrate across two therapeutic inputs—increased signaling through a disease-associated pathway, and the presence of an exogenously-applied, inactive "pro-drug"—to trigger targeted cell death (FIG. 4A).

Figure 4B:
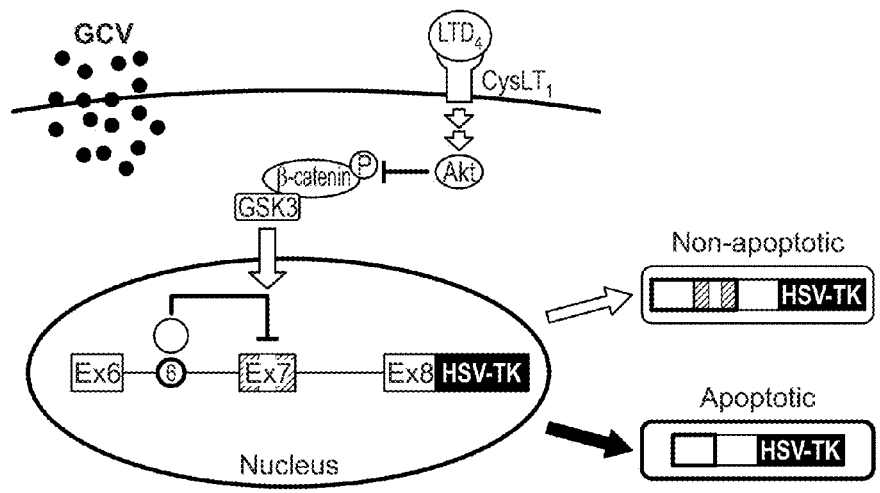
FIGS. 4B and 4C show potential mechanisms of the β-catenin-(β-cat-6) (B) and NF-κB-responsive (p65-3) (C) devices fused to a suicide gene therapy output module (HSV-TK), which control cell survival in response to detection of disease markers and GCV, a pro-drug trigger.
Figure 4C:
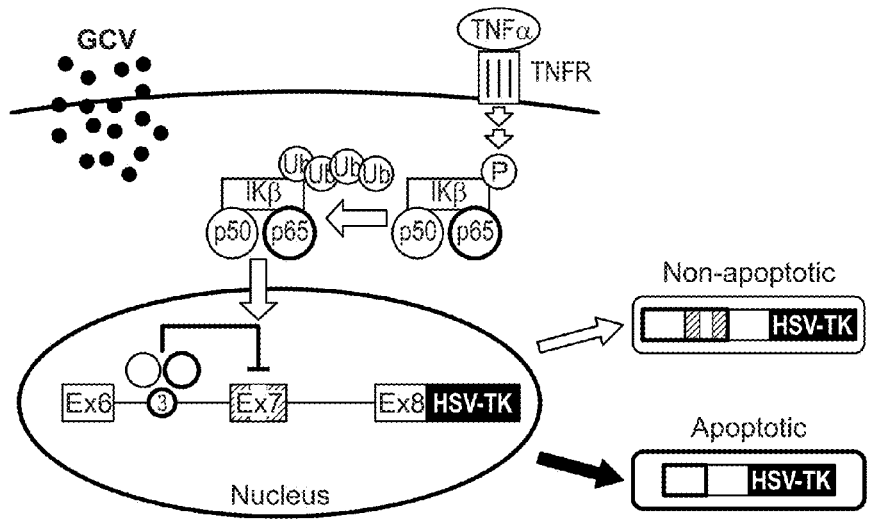
Figure 4D:
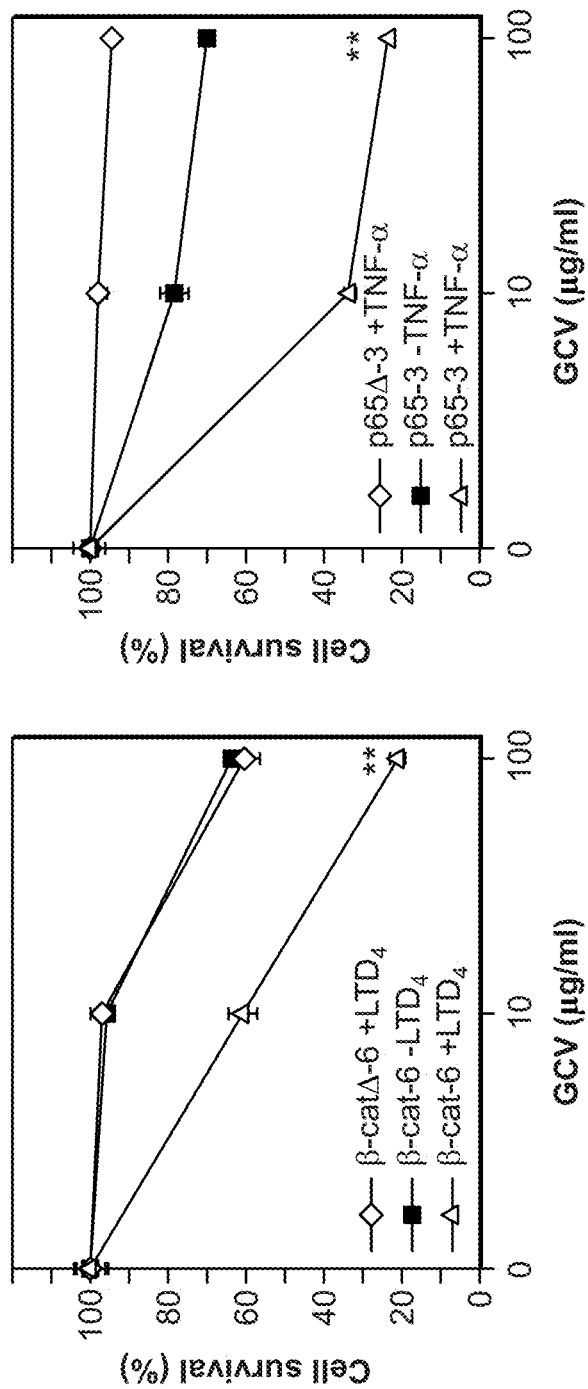
FIG. 4D shows that dose-response curves of cell survival percentages for the β-catenin- and NF-κB-responsive devices fused to HSV-TK indicate a decrease in cell survival as a result of increased signaling through the targeted pathway and the presence of GCV. For all reported data, the mean cell survival levels from two independent experiments are shown.
Figure 8B:
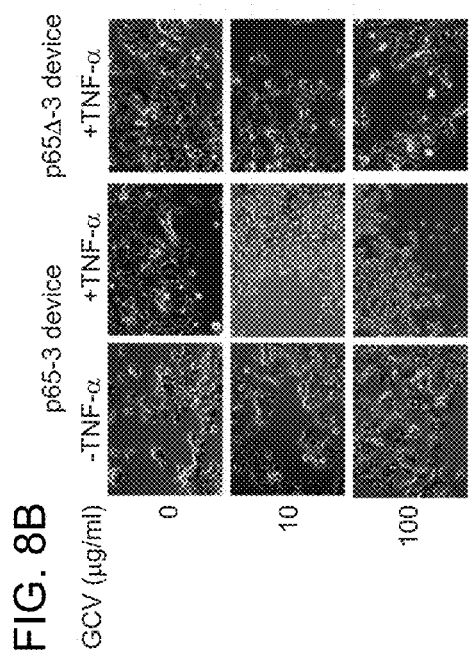
FIGS. 8A and 8B show phase images of the β-catenin-(8A) and NF-κB-responsive (8B) devices fused to HSV-TK. Increased cell death from the β-catenin- and NF-κB-responsive devices is specific to pathway stimulation, GCV, and the wild-type aptamers.
Figure 8A:
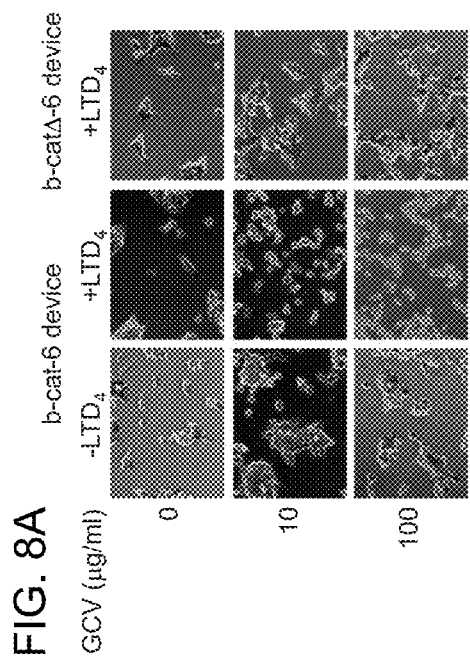
Figure 8D:
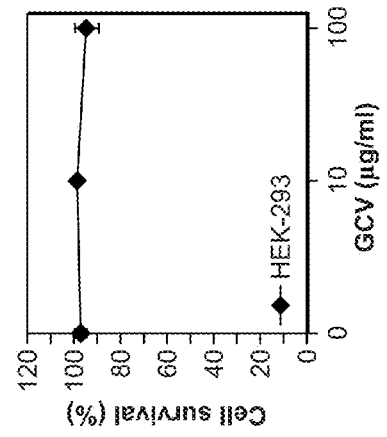
FIG. 8D shows dose-response curve of cell survival percentages for wild-type HEK-293 cells. Survival percentages of cells exposed to GCV (0-100 μg/ml) were assessed by flow cytometry. P-values derived from the Student's t-test for all reported activities are as follows: *P<0.05 and **P<0.01.
Figure 8C:
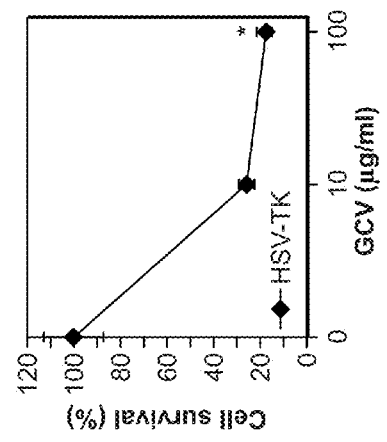
FIG. 8C shows dose-response curve of cell survival percentages for HEK-293 cells stably expressing HSV-TK from a CMV promoter. Survival percentages of cells exposed to GCV (0-100 μg/ml) were assessed by flow cytometry.

To this end, β-catenin- and NF-κB-responsive devices were constructed, such that they are capable of triggering apoptosis by virtue of the replaced output module having a gene encoding the herpes simplex thymidine kinase (HSV-TK) (FIGS. 4B and C). HSV-TK confers sensitivity to the pro-drug ganciclovir (GCV), which induces apoptosis (Beltinger et al., *Proc Natl Acad Sci USA* 96, 8699, 1999) and has been used in clinical trials to treat tumors (Lifang et al., *J Exp Clin Cancer Res* 27, 42, 2008). Cells stably expressing the β-cat-6 and p65-3 devices exhibited increased sensitivity to GCV under pathway stimulation (FIGS. 8A and 8B) and a cell survival of ~20% at 100 µg/ml GCV (P<0.01) (FIG. 4D), similar to that of cells overexpressing HSV-TK (FIG. 8C). Cells expressing the devices in the absence of pathway stimulation and mutant devices under pathway stimulation displayed no observable phenotypic effects and survival rates between 60-90% at 100 µg/ml GCV.

We also demonstrated the modularity of the output function of the device platform by replacing the output module with the proapoptotic gene Puma (FIG. 9).

Example 7

Cell Culture, Transfections, Stable Cell Lines, and Flow Cytometry Analysis

The experiments described in this example pertains to general techniques used in one or more of the examples above, and may have general applicability.

All cell culture media were obtained from Invitrogen. Isogenic HEK-293 stable cell lines were generated by co-transfection of the appropriate RNA device construct and a plasmid encoding the Flp recombinase (pOG44) in HEK-293 FLP-In cells grown in medium without Zeocin according to the manufacturer's instructions (Invitrogen). Stable selections were carried out in 6-well plates seeded with ~2×10⁵

HEK-293 FLP-In cells per well, where 1.8 μg of pOG44 and 0.2 μg of the RNA device construct (10:1 ratio) were co-transfected. Fresh medium was added to the cells 24 h after transfection. The cells were expanded by a 1:4 dilution and Hygromycin B was added to a final concentration of 200 μg/ml 48 h after transfection. Clones were harvested by trypsinization, pooled, and analyzed using a Quanta Cell Lab Cytometer (Beckman Coulter; Fullerton, Calif.) 10-14 days after transfection. Flow cytometry data was analyzed using the FlowJo v.7.1 (Tree Star, Inc.) software package.

Flow cytometry analysis and gating procedures for certain regulatory devices are omitted. However, flow cytometry and gating procedure for the MS2-3-Puma device mediated apoptosis are briefly illustrated below.

Cells were stained with Pacific blue annexin V and 7AAD using the Vybrant Apoptosis Assay Kit (Invitrogen) according to the manufacturer's instructions. The positioning of all gates are based on the individual gates established for each single color control and can vary slightly between experiments. Dot plots show initial gating of all stable cells (P1), followed by gating for all MS2-Venus positive cells. The final gated dot plot reports on the stages of programmed cell death for each cell line using a dual parameter staining consisting of Pacific blue annexin V and 7AAD. Briefly, live cells are Pacific blue annexin V negative and 7AAD negative, apoptotic cells are Pacific blue annexin V positive and 7AAD negative, and dead cells are 7AAD positive. A similar procedure was used for the gating procedure for the β-cat-6-Puma device.

For transient transfection studies, HEK-293 cell lines stably expressing the RNA devices were seeded in 24-well plates at ~5×10$^4$ cells per well 16 to 24 h prior to transfection. Cell lines were transfected with 250 ng of the appropriate MS2-DsRed, MS2-Venus, p50-DsRed, DsRed, or Venus expression constructs. The cells were harvested by trypsinization, pooled, and analyzed by flow cytometry and microscopy 48 h after transfection. All presented microscopy images were taken during an individual experiment. GFP and DsRed fluorescence, as measured by flow cytometry, was excited at 488 nm and emission was measured through a 525-nm filter and a 610-nm band-pass filter, respectively. Experiments were carried out on different days and transfections were completed in duplicate, where the mean GFP fluorescence of the DsRed viable transfected population was evaluated. GFP fluorescence levels of both the wild-type and mutant RNA devices in the presence of ligand were normalized to the GFP fluorescence of the cell lines in the absence of ligand. Relative expression (fold) data is reported as the normalized mean fluorescence for each wild-type sample divided by the normalized mean fluorescence for each mutant sample ±the average error.

For the induction of the Wnt and NF-κB pathways, HEK-293 cell lines stably expressing the RNA devices were seeded in a 24-well plate at ~5×10$^4$ cells per well 16 to 24 h prior to induction with LTD$_4$ or TNF-α. Cells were treated with 20 ng/mL TNF-α (Sigma) for 48 h for the NF-κB pathway induction studies (Hellweg et al., *Ann N Y Acad Sci* 1091, 191, 2006). For the Wnt pathway induction studies, cells were serum starved 2 h before stimulation with 80 nM leukotriene D$_4$ (LTD$_4$) (Sigma) for 48 h in the absence of serum (Mezhybovska et al., *J Biol Chem* 281, 6776, 2006). After stimulation of either pathway, the cells were harvested by trypsinization, pooled and analyzed by flow cytometry and microscopy. GFP fluorescence as measured by flow cytometry was excited at 488 nm and emission was measured through a 525-nm filter band-pass filter. Both microscopy and flow cytometry experiments were carried out on different days and were completed in duplicate, where the mean GFP fluorescence of the viable cell population and the average error between samples is reported. GFP fluorescence levels of both the wild-type and mutant RNA devices in the presence of ligand were normalized to the GFP fluorescence of the cell lines in the absence of ligand. Relative expression (fold) data is reported as the normalized mean fluorescence for each wild-type sample divided by the normalized mean fluorescence for each mutant sample ±the average error.

Example 8

Apoptosis Assays

The experiments described in this example pertains to general techniques used in one or more of the examples above, and may have general applicability.

Stable cell lines were harvested by trypsinization as described above. For the Puma apoptosis studies, cell lines stably expressing the RNA devices were seeded in a 24-well plate at ~5×10$^4$ cells per well 16 to 24 h prior to induction with LTD$_4$ or TNF-α or transfection with 250 ng of MS2-Venus or Venus alone as described above. 48 h after transfection or induction, the pooled cells were washed in cold phosphate-buffered saline (PBS). Cells were stained with Pacific blue annexin V and 7AAD using the Vybrant Apoptosis Assay Kit (Invitrogen) according to the manufacturer's instructions. The fluorescence of the stained cells was measured using a Quanta Cell Lab Cytometer, where the Pacific blue dye was excited using a UV light source and measured through a 465/430 band-pass filter (FL1). Venus and 7AAD were excited with a 488-nm laser and measured through a 535-nm band-pass (FL2) and 670-nm long pass filter (FL3) respectively. In this assay, live cells are annexin V negative and 7AAD negative, apoptotic cells are annexin V positive and 7AAD negative and dead cells are annexin V negative and 7AAD positive. Experiments were carried out on different days and transfections/inductions were completed in duplicate. For the MS2-Puma device studies the mean percentage of cells undergoing apoptosis (annexin V positive and 7AAD negative) within the Venus positive population ±the average error is reported. For the NF-κB and Wnt signaling devices fused to Puma, the mean percentage of cells undergoing apoptosis (annexin V positive and 7AAD negative) ±the average error is reported. Flow cytometry analysis and gating procedures for some apoptosis-inducing regulatory devices are omitted.

For the ganciclovir (GCV) sensitivity assays, HEK-293 cell lines stably expressing the RNA devices were seeded in a 24-well plate at ~5×10$^4$ cells per well 16 to 24 h prior to induction with LTD$_4$ or TNF-α. At the time of induction cells were either left untreated or incubated with different concentrations of GCV (10 or 100 μg/ml). After 96 h the cells were harvested by trypsinization, pooled and analyzed by flow cytometry and microscopy. For these studies, the mean percentage of alive cells (7AAD negative) ±the average error is reported.

Example 9 qRT-PCR Analysis

The experiments described in this example pertains to general techniques used in one or more of the examples above, and may have general applicability.

Total cellular RNA was purified from stably transfected HEK-293 Flp-In cells using GenElute mammalian total RNA purification kit (Sigma) according to the manufacturer's instructions, followed by DNase treatment (Invitrogen). cDNA was synthesized using a gene-specific primer for the pcDNA5/FRT vector (SMN1cDNA) and Superscript III reverse transcriptase (Invitrogen) according to the manufacturer's instructions. qRT-PCR analysis was performed using isoform-specific primers (see "isoform-specific primers table" below) where each reaction contained 1 μL template cDNA, 10 pmol of each primer, and 1× iQ SYBR green supermix (BioRAD) to a final volume of 25 μL.

more concerned with the absolute performance of the device. Therefore, we report absolute measures of cell survival (or death) within a given cell population for the phenotypic assays and do not report values normalized to the relevant negative control. The negative controls are reported separately to demonstrate the specificity of ligand addition on the resulting phenotypic effect to cells harboring the functional devices. These assays demonstrate that the RNA devices are able to effectively regulate a phenotypic response in a manner that correlates with their characterized gene-regulatory activ-

| Name | Forward Primer (5'-3') | Reverse Primer (5'-3') | Isoform |
|---|---|---|---|
| Pair 1 | GTATTATATGGAAATGCTGG | GAA GGTGGTCACGAGGG | Ex6/8 and GFP |
| Pair 2 | TAAATTAAGGAGAAATGCT | GAA GGTGGTCACGAGGG | Ex7/8 and GFP |
| Pair 3 | CAAAGATGGTCAAGGTCGCAAG | GGCGATGTCAATAGGACTCC | HPRT |

Reactions were carried out using a iCycler iQ system (BioRAD) for 30 cycles (95° C. for 15 s, 72° C. for 30 s). The purity of the PCR products was determined by melt curve analysis. Data analysis was completed using the iCycler IQ system software v.3.1.7050 (BioRAD). Isoform-specific relative expression was calculated using the ΔCt (change in cycling threshold) (Livak and Schmittgen, Methods 25, 402, 2001). Expression levels of duplicate PCR samples were normalized to the levels of HPRT (Hypoxanthine-guanine phosphoribosyltransferase). Unless otherwise noted, data is reported as the ratio of the mean expression levels of the exon 7 excluded isoform to the exon 7 included isoform for the wild-type device relative to the same ratio for the mutant control device under the indicated ligand condition ±the average error.

The device responses are characterized through several different gene expression and phenotypic assays, such as those described in the several examples above, and the reproducible agreement between these characterization methods provide further confirmation of their ligand-responsive gene-regulatory activities. Specifically, activity measurements based on transcript isoform (assayed through qRT-PCR) and fluorescent reporter levels (assayed through flow cytometry) generally agree with one another. In addition, for the majority of the devices, the characterized device response is apparent in the unnormalized data for both fluorescent reporter and transcript isoform levels. The exception to this are for the devices that increase exon inclusion (MS2-6 and the NF-κB p50-responsive devices), where unnormalized gene expression data indicate no changes or slight increases in GFP levels in the presence of ligand. However, the fold change in GFP levels is significantly lower than all devices that increase exon exclusion, and the corresponding unnormalized transcript isoform levels support the reported device responses. The transcript isoform levels provide a more direct measure of splicing regulation from the devices, whereas cellular fluorescence is likely more influenced by any nonspecific effects of the ligands.

Finally, the ligand-specific responses of the devices are further supported by phenotypic assays that characterize cell survival and cell death within cell populations harboring individual devices in the presence and absence of appropriate ligands (FIG. 4). In a therapeutic application one would be ity. In addition, the data demonstrate that relatively moderate gene-regulatory effects (~2-4-fold) can be used to effectively regulate downstream functional outputs when linked to potent upstream regulators. This observation is supported by other recent work on engineered RNA regulatory systems applied to the regulation of T-cell proliferation (Chen et al., Proc Natl Acad Sci USA, 107, 8531, 2010) and bacterial chemotaxis (Sinha et al., Nat Chem Biol 6, 464, 2010).

Example 10

Statistical Analysis

The experiments described in this example pertains to general techniques used in one or more of the examples above, and may have general applicability.

Data are expressed as relative expression (fold) or expression (fold) ±average error where applicable. Relative expression (fold) is taken to be: [(device response (+ligand))/(device response (−ligand))]/[(mutant device response (+ligand))/(mutant device response (−ligand))] or is the ratio of the expression of the wild-type device in the presence of ligand to the absence of ligand, normalized to the same ratio for the mutant RNA device. Expression (fold) is the ratio of the expression of the RNA device in the presence of ligand to the absence of ligand. Relative expression is the ratio of the expression of the wild-type device to the mutant device under the same condition. Student's t-test and Anova analyses were performed using Microsoft Excel. $P<0.05$ were taken to be significant.

In summary, the results in the examples above demonstrate that the subject RNA devices can effectively rewire signaling through disease-associated pathways to trigger apoptosis using clinically-relevant genetic systems. There was a slight reduction in survival in cells expressing the subject devices in the absence of pathway stimulation, which may reflect effects of high GCV concentrations on cell viability (FIG. 8D) (Song et al., Int J Gynecol Cancer 16, 156, 2006) and basal expression of HSV-TK from the subject devices. Possible therapeutic utility and safety of these targeted cell death devices is supported by effective cell-killing efficacy in the presence of both inputs and minimal background activity in the absence of one or both inputs. These results demonstrate that synthetic RNA controllers with moderate gene regulatory activities (~2-4-fold) can achieve substantial alterations in downstream functional behaviors through their coupling to potent genetic targets, and effects that are amplified through associated cellular pathways.

The system described herein demonstrates that both heterologous and endogenous proteins not associated with splicing regulation can be directed to alter splicing patterns through synthetic protein-binding sequences. In contrast to protein-based transcriptional control systems, RNA-based systems present advantages in enabling response to proteins other than transcription factors, direct tailoring of input/output processing functions without device redesign, extension to combinatorial processing, and practical implementation in clinical applications (Win et al., *Chem Biol* 16, 298, 2009; Chen et al., *Proc Natl Acad Sci USA*, 107, 8531, 2010). The application of the subject devices to the processing of multiple protein inputs can be used to engineer RNA-based devices with sophisticated information processing activities and to design and build complex regulatory networks to interrogate and program cellular function.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EQUIVALENTS

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

The invention claimed is:

1. An RNA capable of undergoing alternative splicing in an actuator module, comprising:
   (1) an input module comprising an aptamer that binds a protein ligand not associated with splicing regulation;
   (2) an output module comprising a coding sequence for a functional gene product; and,
   (3) the actuator module operably connected to the input module and the output module, and said actuator module comprising a sequence capable of undergoing alternative splicing,
   wherein the aptamer is integrated into the actuator module and into an intron, and is integrated between 1 and 50 nt away from a regulatory sequence for alternative splicing, and wherein binding of the protein ligand to the aptamer enhances or inhibits the function of the regulatory sequence to alter alternative splicing pattern and expression of the coding sequence.

2. The RNA of claim 1, wherein the regulatory sequence is a 5' splice site (5' ss), a 3' splice site (3' ss), a splicing branch point, a polypyrimidine tract, a splicing enhancer, or a splicing suppressor.

3. The RNA of claim 1, wherein the protein ligand is endogenous to a cell.

4. The RNA of claim 1, wherein the protein ligand contains a nuclear localization sequence.

5. The RNA of claim 1, wherein expressing of the protein ligand or lack thereof is associated with an abnormal or a differentiated state of a cell.

6. The RNA of claim 5, wherein the abnormal state is associated with a disease condition, over-proliferation of a cell, drug resistance, or abnormal apoptosis.

7. The RNA of claim 1, wherein the sequence capable of undergoing alternative splicing is a minigene comprising a first exon, a first intron, a second exon, a second intron, and a third exon in tandem, wherein the second exon is included in one alternative splicing product, but is excluded in a different alternative splicing product.

8. The RNA of claim 7, wherein the second exon comprises a sequence element that inhibits the expression of a product encoded by the coding sequence.

9. The RNA of claim 8, wherein the sequence element is a translation stop codon, a transcription terminator, a secondary structure that inhibits ribosome function, or a self-cleaving ribozyme.

10. The RNA of claim 1, wherein the aptamer is integrated between 2 and 30 nt away from the regulatory sequence.

11. The RNA of claim 1, wherein the aptamer is integrated between 2 and 20 nt away from the regulatory sequence.

12. The RNA of claim 1, wherein the output module is 3' to the actuator module.

13. The RNA of claim 1, comprising modified nucleotide and/or sugar-phosphate backbone.

14. The RNA of claim 1, wherein the coding sequence encodes a reporter protein, a transcription factor, an enzyme, a proapoptotic protein, or an anti-apoptotic protein.

15. An RNA capable of undergoing alternative splicing in an actuator module, comprising:
   (1) a first input module comprising a first aptamer that binds a first protein ligand not associated with splicing regulation, and integrated into an intron, at or near a first regulatory sequence for alternative splicing;
   (2) a second input module comprising a second aptamer that binds a second protein ligand, and integrated into the intron, at or near a second regulatory sequence for alternative splicing;
   (3) an output module comprising a coding sequence; and,
   (4) the actuator module operably connected to the first and second input modules and the output module, and said actuator module comprising a sequence capable of undergoing alternative splicing,
   wherein binding of the first and second protein ligands to their respective aptamers synergistically modulates alternative splicing through modulating the function of the respective regulatory sequences.

16. The RNA of claim 15, wherein the first and second aptamers are different.

17. The RNA of claim 15, wherein the first and second protein ligands are different.

18. A method of producing a desired RNA capable of undergoing alternative splicing in an actuator module, the method comprising:
   (1) providing a candidate RNA comprising:
      (a) an input module comprising an aptamer that binds a protein ligand not associated with splicing regulation;
      (b) an output module comprising a coding sequence; and,
      (c) the actuator module operably connected to the input module and the output module,
      wherein the aptamer is integrated into the actuator module and into an intron, and is integrated at an integration site that is between 1-50 nt away from a regulatory sequence for alternative splicing;
   (2) contacting each RNA with the protein ligand, under a condition that permits binding of the protein ligand to the aptamer;
   (3) determining whether binding of the protein ligand to the aptamer integrated at the integration site enhances or inhibits the function of the regulatory sequence in alternative splicing;

(4) isolating the candidate RNA as the desired RNA, if binding of the protein ligand to the aptamer either enhances or inhibits the function of the regulatory sequence in alternative splicing.

19. The method of claim 18, further comprising replacing the aptamer with a different aptamer, and repeating steps (2)-(4).

20. The method of claim 19, wherein the different aptamer binds to a different protein ligand.

* * * * *

UNITED STATES PATENT AND TRADEMARK OFFICE
CERTIFICATE OF CORRECTION

PATENT NO. : 8,604,176 B2  
APPLICATION NO. : 12/943350  
DATED : December 10, 2013  
INVENTOR(S) : Christina D. Smolke et al.

Page 1 of 1

It is certified that error appears in the above-identified patent and that said Letters Patent is hereby corrected as shown below:

In the Specification

On Column 1, Lines 13-16, immediately below the Section entitled "GOVERNMENT SUPPORT," please replace the original paragraph below:
"Work described herein was funded, in whole or in part, by R21 CA115471-01 and 1RC1 GM091298-01 from the National Institute of Health (NIH). The United States Government has certain rights in this invention."
With:
--This invention was made with government support under Grant No. CA115471 awarded by the National Institutes of Health (NIH). The government has certain rights in the invention.--

Signed and Sealed this  
Sixth Day of October, 2020

Andrei Iancu  
*Director of the United States Patent and Trademark Office*

SEQUENCE LISTING

```
<160> NUMBER OF SEQ ID NOS: 76

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtacaccat cagggtacg                                                19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgtacccatc agggtacg                                                 18

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aggccgatct atggacgcta taggcacacc ggatacttta acgattggct              50
```

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tcggttagca atttcatagg ccacacggat atcgcaggta tctagccgga        50

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
gcatcctgaa actgttttaa ggttggccga tgc        33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
cgtagccggt tggaattttg tcaaagtcct acg        33

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gatcttgaaa ctgttttaag gttggccgat c        31

<210> SEQ ID NO 9
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
gaagcttaca agaaggacag cacgaataaa acctgcgtaa atccgcccca tttgtgtaag        60
ggtagtgggt cgaattccgc tca        83

<210> SEQ ID NO 10
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
actcgcctta agctgggtga tgggaatgtg tttaccccgc ctaaatgcgt ccaaaataag        60

```
cacgacagga agaacattcg aag                                              83
```

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gcgcgctagc atgtattata tggtaagtaa tcactcagc                             39
```

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
atagctagcg ctgctacctg ccagc                                            25
```

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gcgcgctagc gtgagcaagg gcgag                                            25
```

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gcgcgggccc ttagtacagc tcgtccatgc c                                     31
```

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
atagtttaaa cggtggttct ggtggttctg cccgcgcacg ccaggag                    47
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
gcgcgtttaa acttaattgg gctccatctc ggg                                   33
```

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcgcgctagc gtgacagggg gaatggc                                         27

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgcgtttaa acttagttag cctcccccat ctc                                  33

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ataggatccg acaacaccga ggacgtcat                                       29

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atagcggccg cctactggga gccggag                                         27

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agccaaaaaa aaaacgcaaa gtggcttcta actttactca gttcgttc                  48

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ataggatcca ccaccaccac cgtagatgcc g                                    31

```
<210> SEQ ID NO 23
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ataggtacca tggattacaa ggatgacgat gacaagccaa aaaaaaaacg caaagtggct      60
tctaacttta c                                                          71

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agccaaaaaa aaaacgcaaa gtggcagaag atgatccata tttgggaag                 49

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ataggtaccg tcatcactttt tgtcacaacc ttc                                 33

<210> SEQ ID NO 26
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atagctagca tggattacaa ggatgacgat gacaagccaa aaaaaaaacg caaagtggca      60
gaagatgatc c                                                          71

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tagaaggcac agtcgagg                                                   18

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atatgatact agctatcagg ccga                                            24
```

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
atatgatatc tagctatctc ggttag                                            26

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
atatatcgat gtctatatag ctattttttt taactt                                 36

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
atatatcgat gtctatatag ctattttttt taactt                                 36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
atactcgagc agacttactc cttaatttaa ggaatg                                 36

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
atatgatatc tagctatccg cgc                                               23

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
atatgatatc tagctatccg tagcc                                             25

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atatgatatc tagctatccg cgc                                          23

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atatgatatc tagctatcga agctacaaga aggacagcac                        40

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atatggtacc aacacgtaca ccatcagggt acgtccatat aaagctatag atatctagct   60
atcgatatat                                                         70

<210> SEQ ID NO 38
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atatggtacc aacacgtacc catcagggta cgtccatata agctataga tatctagcta    60 tcgatatat                                                          69

<210> SEQ ID NO 39
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atatggtacc aacatccata taaagctatc gtacaccatc agggtacgag atatctagct   60
atcgattat                                                          69

<210> SEQ ID NO 40
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atatggtacc aacatccata taaagctatc gtacccatca gggtacgaga tatctagcta    60
tcgattat                                                             68

<210> SEQ ID NO 41
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atatgatatc tagctatccg tacaccatca gggtacggat gtctatatag ctattttttt    60
taacttcctt tattttcctt acagggtttc agacaaaatc aaaagaagg aaggtgctca    120 cattccttaa attaaggagt aagtctgctc gagatat                            157

<210> SEQ ID NO 42
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atatgatatc tagctatccg tacccatcag ggtacggatg tctatatagc tatttttttt    60
aacttccttt attttcctta cagggtttca gacaaaatca aaagaagga aggtgctcac    120 attccttaaa ttaaggagta agtctgctcg agatat                             156

<210> SEQ ID NO 43
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atatatcgat gtctatatag ctcgtacacc atcaggtacg atttttttta acttccttta    60
ttttccttac agggtttcag acaaaatcaa aagaaggaa ggtgctcaca ttccttaaat    120
taaggagtaa gtctgctcga gatat                                         145

<210> SEQ ID NO 44
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atatatcgat gtctatatag ctcgtaccca tcagggtacg atttttttta acttccttta    60
ttttccttac agggtttcag acaaaatcaa aagaaggaa ggtgctcaca ttccttaaat    120
taaggagtaa gtctgctcga gatat                                         145

<210> SEQ ID NO 45
<211> LENGTH: 146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
atatatcgat gtctatatag ctattttttt taacttccgt acaccatcag ggtacgcttt    60
attttcctta cagggtttca gacaaaatca aaaagaagga aggtgctcac attccttaaa   120
ttaaggagta agtctgctcg agatat                                        146
```

<210> SEQ ID NO 46
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
atatatcgat gtctatatag ctattttttt taacttccgt acccatcagg gtacgcttta    60
ttttccttac agggtttcag acaaaatcaa aagaaggaa ggtgctcaca ttccttaaat    120
taaggagtaa gtctgctcga gatat                                         145
```

<210> SEQ ID NO 47
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atatatcgat gtctatatag ctattttttt taacttcctt tattttcctt accgtacacc    60
atcagggtac gagggtttca gacaaaatca aaaagaagga aggtgctcac attccttaaa   120
ttaaggagta agtctgctcg agatat                                        146
```

<210> SEQ ID NO 48
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
atatatcgat gtctatatag ctattttttt taacttcctt tattttcctt accgtaccca    60
tcagggtacg agggtttcag acaaaatcaa aagaaggaa ggtgctcaca ttccttaaat    120
taaggagtaa gtctgctcga gatat                                         145
```

<210> SEQ ID NO 49
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atatatcgat gtctatatag ctattttttt taacttcctt tattttcctt acagggtttc    60
agacaaaatc aaaaagaagg aaggtgctca cattccttaa attaaggagt aagtctgcgt   120
acaccatcag ggtacgctcg agatat                                        146
```

<210> SEQ ID NO 50

```
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atatatcgat gtctatatag ctatttttt taacttcctt tattttcctt acagggtttc      60
agacaaaatc aaaagaagg aaggtgctca cattccttaa attaaggagt aagtctgcgt     120
acccatcagg gtacgctcga gatat                                          145

<210> SEQ ID NO 51
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atatctcgag ccagcattac gtacaccatc agggtacgtg aaagtgaatc ttacttttgt     60
aaaaaagctt atat                                                      74

<210> SEQ ID NO 52
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atatctcgag ccagcattac gtacccatca gggtacgtga aagtgaatct tacttttgta     60
aaaaagctta tat                                                       73

<210> SEQ ID NO 53
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atatctcgag ccagcattat gaaagtgaat cttacgtaca ccatcagggt acgcttttgt     60
aaaaaagctt atat                                                      74

<210> SEQ ID NO 54
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atatctcgag ccagcattat gaaagtgaat cttacgtacc catcagggta cgcttttgta     60
aaaaagctta tat                                                       73

<210> SEQ ID NO 55
<211> LENGTH: 94
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 55
atatctcgag ccagcattat gaaagtgaat cttacttttg taaaaaagcc gtacaccatc    60
agggtacgtt ctttatggtt tgtgggatcc atat                                94

<210> SEQ ID NO 56
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atatctcgag ccagcattat gaaagtgaat cttacttttg taaaaaagcc gtacccatca    60
gggtacgttc tttatggttt gtgggatcca tat                                 93

<210> SEQ ID NO 57
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atataagctt ctttatggtt tgtcgtacac catcagggta cggggatcca tat           53

<210> SEQ ID NO 58
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atataagctt ctttatggtt tgtcgtaccc atcagggtac ggggggatcca tat          53

<210> SEQ ID NO 59
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atatggatcc aaatgtttcg tacaccatca gggtacgttg aacagttaat ctagaatat     59

<210> SEQ ID NO 60
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atatggatcc aaatgtttcg tacccatcag ggtacgttga acagttaatc tagaatat      58

<210> SEQ ID NO 61
<211> LENGTH: 188

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atatgatatc tagctatcag gccgatctat ggacgctata ggcacaccgg atactttaac    60
gattggctga tgtctatata gctattttt ttaacttcct ttattttcct tacagggttt   120
cagacaaaat caaaagaag gaaggtgctc acattcctta aattaaggag taagtctgct   180
cgagatat                                                            188

<210> SEQ ID NO 62
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atatgatatc tagctatctc ggttagcaat ttcataggcc acacggatat cgcaggtatc    60
tagccggaga tgtctatata gctattttt ttaacttcct ttattttcct tacagggttt   120
cagacaaaat caaaagaag gaaggtgctc acattcctta aattaaggag taagtctgct   180
cgagatat                                                            188

<210> SEQ ID NO 63
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atatatcgat gtctatatag ctattttt taacttcctt tattttcctt acaggccgat     60
ctatggacgc tataggcaca ccggatactt taacgattgg ctagggttc agacaaaatc   120 aaaagaagg aaggtgctca cattccttaa attaaggagt aagtctgctc gagatat      177

<210> SEQ ID NO 64
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atatatcgat gtctatatag ctattttt taacttcctt tattttcctt actcggttag     60
caatttcata ggccacacgg atatcgcagg tatctagccg gaagggtttc agacaaaatc  120 aaaagaagg aaggtgctca cattccttaa attaaggagt aagtctgctc gagatat      177

<210> SEQ ID NO 65
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
```

```
atatgatatc tagctatcgc atcctgaaac tgttttaagg ttggccgatg cgatgtctat      60
atagctattt ttttaacttt cctttatttt ccttacaggg tttcagacaa aatcaaaaag     120
aaggaaggtg ctcacattcc ttaaattaag gagtaagtct gctcgagata t              171
```

<210> SEQ ID NO 66
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
atatgatatc tagctatccg tagccggttg gaattttgtc aaagtcctac ggatgtctat      60
atagctattt ttttaacttt cctttatttt ccttacaggg tttcagacaa aatcaaaaag     120
aaggaaggtg ctcacattcc ttaaattaag gagtaagtct gctcgagata t              171
```

<210> SEQ ID NO 67
<211> LENGTH: 179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
atatgatatc tagctatccg cgcgatcttg aaactgtttt aaggttggcc gatcgcgcgg      60
atgtctatat agctatttt tttaacttcc tttattttcc ttacagggtt tcagacaaaa     120
tcaaaaagaa ggaaggtgct cacattcctt aaattaagga gtaagtctgc tcgagatat     179
```

<210> SEQ ID NO 68
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gaagcttaca agaaggacag cacgaataaa acctgcgtaa atccgcccca tttgtgtaag      60
ggtagtgggt cgaattccgc tcagatgtct atatagctat tttttttaac ttcctttatt     120
ttccttacag ggtttcagac aaaatcaaaa agaaggaagg tgctcacatt ccttaaatta     180
aggagtaag                                                             189
```

<210> SEQ ID NO 69
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
actcgcctta agctgggtga tgggaatgtg tttaccccgc taaatgcgt ccaaaataag       60 cacgacagga agaacattcg aaggatgtct atatagctat tttttttaac ttcctttatt     120
ttccttacag ggtttcagac aaaatcaaaa agaaggaagg tgctcacatt ccttaaatta     180
aggagtaag                                                             189
```

<210> SEQ ID NO 70

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Ser Gly Gly Ser
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Tyr Lys Asp Asp Asp Asp Lys
1               5

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtattatatg gaaatgctgg                                              20

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gaaggtggtc acgaggg                                                 17

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
taaattaagg agaaatgct                                               19

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 75
caaagatggt caaggtcgca ag                                           22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggcgatgtca ataggactcc                                              20
```